United States Patent
Wrolstad et al.

(10) Patent No.: US 12,186,131 B2
(45) Date of Patent: Jan. 7, 2025

(54) INTRALUMINAL ULTRASOUND ASSEMBLY HAVING A MULTIPLE MATERIAL SUPPORT MEMBER, AND ASSOCIATED DEVICES, SYSTEMS, AND METHODS

(71) Applicant: KONINKLIJKE PHILIPS N.V., Eindhoven (NL)

(72) Inventors: David Kenneth Wrolstad, Fallbrook, CA (US); Maritess Minas, San Diego, CA (US); Nathan Andrew Williams, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 266 days.

(21) Appl. No.: 17/763,864

(22) PCT Filed: Sep. 30, 2020

(86) PCT No.: PCT/EP2020/077277
§ 371 (c)(1),
(2) Date: Mar. 25, 2022

(87) PCT Pub. No.: WO2021/069262
PCT Pub. Date: Apr. 15, 2021

(65) Prior Publication Data
US 2022/0330916 A1     Oct. 20, 2022

Related U.S. Application Data

(60) Provisional application No. 62/912,339, filed on Oct. 8, 2019.

(51) Int. Cl.
*A61B 8/00*     (2006.01)
*A61B 8/12*     (2006.01)

(52) U.S. Cl.
CPC ............. *A61B 8/445* (2013.01); *A61B 8/12* (2013.01)

(58) Field of Classification Search
CPC ..... A61B 8/445; A61B 8/12; A61B 2090/378; A61B 17/2202
See application file for complete search history.

(56) References Cited

U.S. PATENT DOCUMENTS 6,776,763 B2   8/2004  Nix
7,226,417 B1   6/2007  Eberle
(Continued)

FOREIGN PATENT DOCUMENTS

WO   WO-2017167883 A1 * 10/2017   ............... A61B 8/12

OTHER PUBLICATIONS

International Search Report and Written Opinion of PCT/P2020/077277, dated Jan. 22, 2021.

*Primary Examiner* — Gerald Johnson

(57) ABSTRACT

An intravascular imaging probe including a multiple material support member or chassis, and associated devices, systems, and methods are provided. According to one embodiment, an intraluminal ultrasound imaging catheter includes a flexible elongate member configured to be positioned within a body lumen of a patient, a support member coupled to a distal portion of the flexible elongate member, and an ultrasound scanner assembly positioned around the support member. The support member includes a hollow inner member comprising a first material, and a first annular member positioned around a perimeter of the hollow inner member at a proximal portion of the hollow inner member. The first annular member extends radially outward from the hollow inner member and includes a second material that is different from the first material.

22 Claims, 20 Drawing Sheets

(56) References Cited

U.S. PATENT DOCUMENTS

| | | | |
|---|---|---|---|
| 2004/0044286 A1 | 3/2004 | Hossack | |
| 2010/0262014 A1* | 10/2010 | Huang | A61B 8/12 |
| | | | 600/466 |
| 2015/0305710 A1 | 10/2015 | Stigall | |
| 2016/0029999 A1* | 2/2016 | Corl | A61B 8/5207 |
| | | | 600/463 |
| 2019/0231313 A1 | 8/2019 | Saroha | |
| 2020/0297306 A1 | 9/2020 | Wrolstad | |
| 2020/0397403 A1 | 12/2020 | Minas | |

* cited by examiner

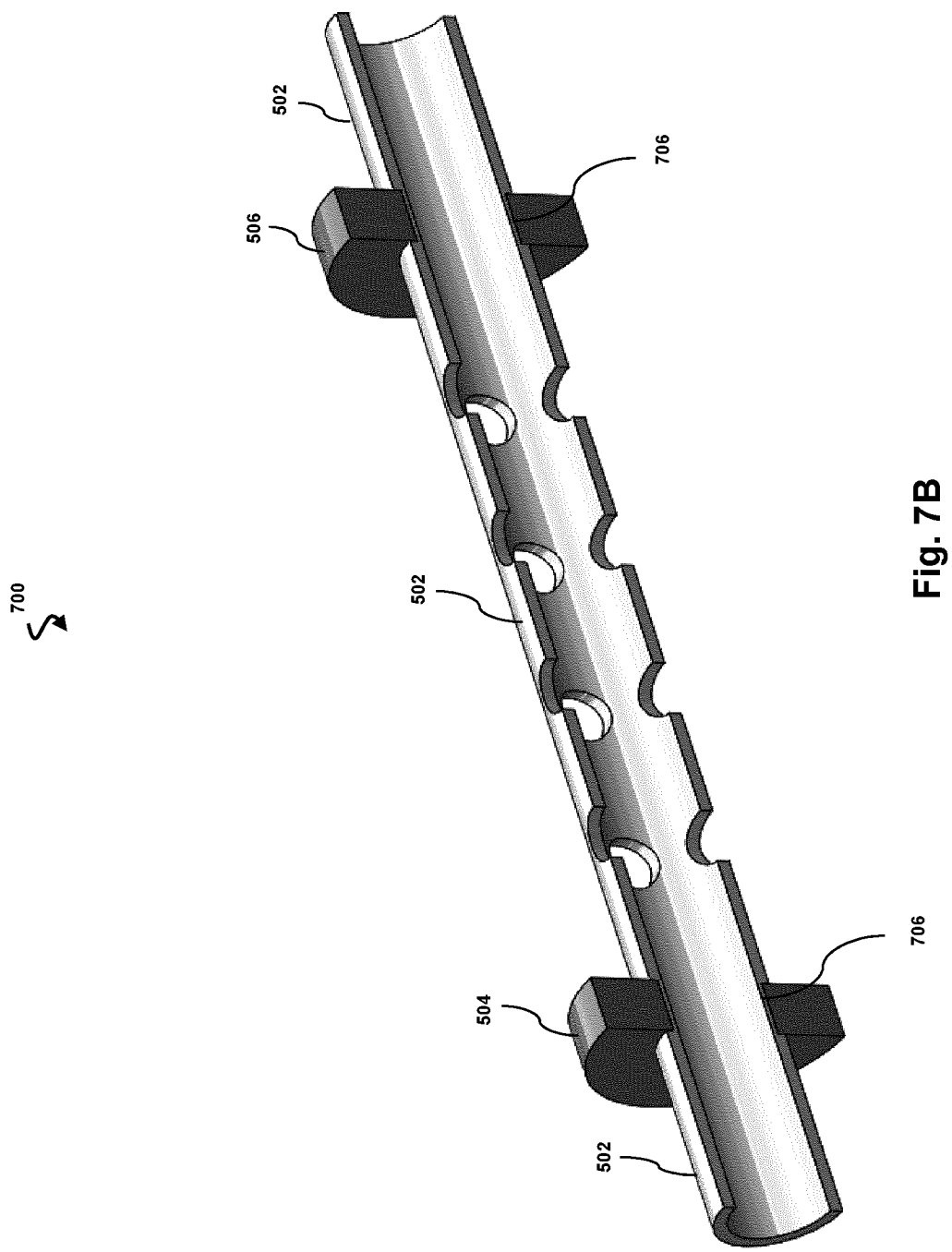

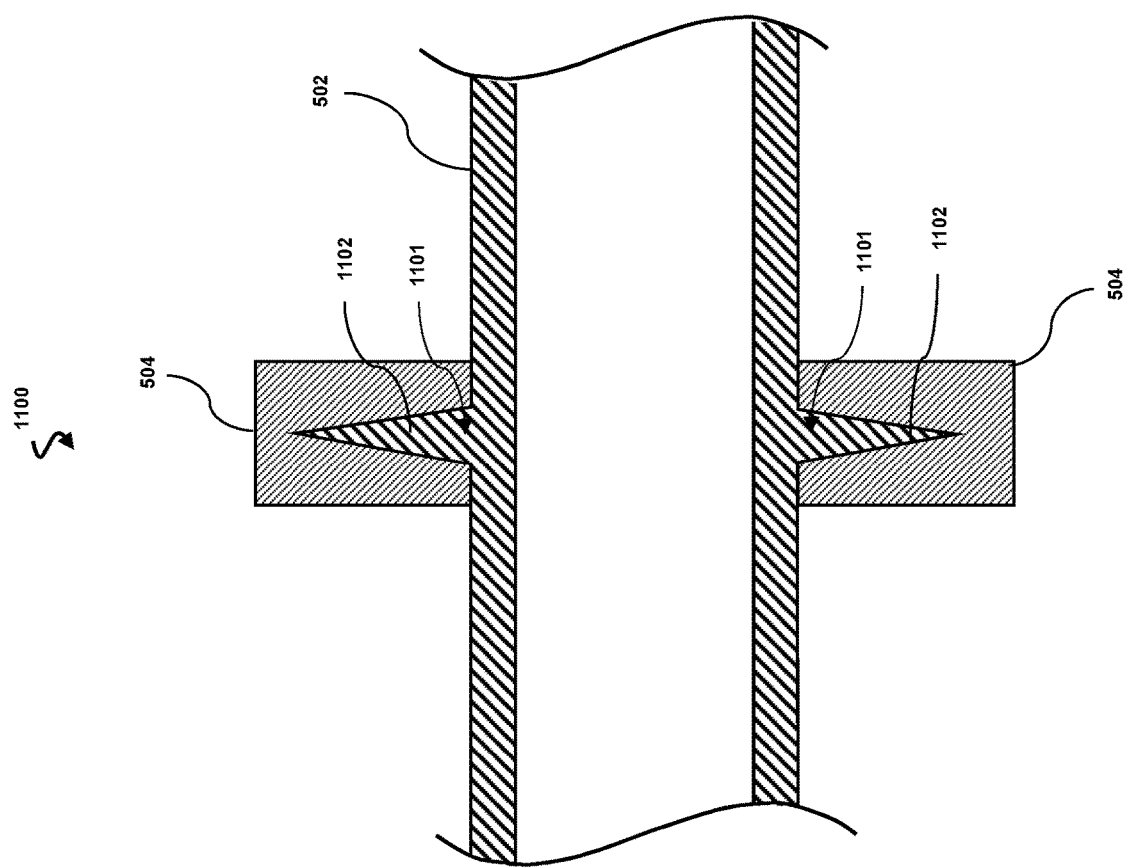

INTRALUMINAL ULTRASOUND ASSEMBLY HAVING A MULTIPLE MATERIAL SUPPORT MEMBER, AND ASSOCIATED DEVICES, SYSTEMS, AND METHODS

TECHNICAL FIELD

The present disclosure relates generally to the structural arrangement of an intravascular ultrasound device, and in particular, to an intravascular ultrasound device with a support member formed of multiple materials to provide structural support and other mechanical properties to the device.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers distributed around its circumference along with one or more integrated circuit controller chips mounted adjacent to the transducer array. The controllers select individual acoustic elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

When designing an IVUS device it is important to take into consideration practical limitations such as manufacturability, reliability, resiliency and mechanical performance. It is desirable that the ultrasound catheter assembly produce high quality raw image signals for the signal processing system located outside the body within which the intravascular ultrasound transducer assembly is inserted for imaging. However, there is an interest in limiting the number of parts since added complexity can increase the manufacturing costs and reduce the yield of the intravascular ultrasound catheter assemblies. It is desirable that the devices be sufficiently resilient and have sufficient structural support to navigate tortuous regions of the vasculature without damaging the electronic components of the IVUS device.

Conventional IVUS devices include a support member, which may also be referred to as a chassis, or a unibody, formed of a metal tube. An ultrasound imaging assembly is positioned over or around the support member. The support member provides structural support, rigidity, radiopacity and other characteristics to the scanner assembly. Conventional support members suffer from a number of drawbacks. For example, the manufacturing techniques available for metals (e.g., milling, welding, etc.) limit the geometric configuration of support members that can be produced. Similarly, steel cannot be re-flowed with polymers and does not effectively scatter or attenuate ultrasound waves. Accordingly, conventional support members constructions may limit mechanical and/or acoustic performance of IVUS devices.

SUMMARY

The present application provides an improved intravascular imaging probe that includes a multiple material support member or chassis as part of the imaging assembly at the distal portion of the IVUS catheter. The support member is formed from multiple (i.e. two, three, or more) materials with various structural complexities. The chassis may include a cylindrical hollow core or a hypotube combined with polymer features over molded, fitted, or otherwise coupled directly to the hollow core. The multi material construction allows for features to be directly molded or coupled to the support structure, which may improve and/or simplify the manufacturing process, and may provide for more varied geometrical configurations that exhibit improved mechanical and/or acoustic performance. In some aspects, the multi-material chassis may have rigid structures to prevent any stresses imposed on the sensor components and more flexible structures to increase the resilience and maneuverability of the IVUS catheter.

According to an embodiment of the present disclosure, an intraluminal ultrasound imaging catheter includes: a flexible elongate member configured to be positioned within a body lumen of a patient; a support member coupled to a distal portion of the flexible elongate member. In some embodiments, the support member includes: a hollow inner member comprising a first material; a first annular member positioned around a perimeter of the hollow inner member at a proximal portion of the hollow inner member, wherein the first annular member extends radially outward from the hollow inner member, and wherein the first annular member comprises a second material that is different from the first material. In some embodiments, the intraluminal ultrasound imaging catheter further includes an ultrasound scanner assembly positioned around the first annular member of the support member, wherein the ultrasound scanner assembly is configured to obtain ultrasound imaging data of the body lumen.

In some embodiments, the hollow inner member comprises a cylindrical shape. In some embodiments, the hollow inner member comprises a uniform outer surface and a uniform inner surface. In some embodiments, the hollow inner member comprises an outer surface with a first recess, and the first recess is formed at the proximal portion of the hollow inner member such that the second material of the first annular member is positioned within the first recess. In some embodiments, the first material of the hollow inner member comprises a metal and the second material of the first annular member comprises a polymer. In some embodiments, the second material is over molded onto the hollow inner member. In some embodiments, the first annular member comprises a ring shape. In some embodiments, the first annular member comprises a polygonal shape. In some embodiments, the hollow inner member and the first annular member are coupled by an adhesive at the proximal portion of the hollow inner member. In some embodiments, the adhesive comprises a polymer material.

In some embodiments, the support member further comprises a sleeve member positioned around the perimeter of the hollow inner member at an intermediate portion of the inner hollow member. In some embodiments, the sleeve member is positioned distal of the first annular member. In some embodiments, the sleeve member comprises a third material. In some embodiments, the hollow inner member comprises an outer surface with a second recess. In some embodiments, the second recess is formed at the intermediate portion of the hollow inner member such that the sleeve member is positioned within the second recess to form a continuous outer profile with the hollow inner member. In some embodiments, the third material of the sleeve member comprises a polymer. In some embodiments, the support member further comprises a second annular member positioned around the perimeter of the hollow inner member at a distal portion of the hollow inner member. In some embodiments, the second annular member extends radially outward from the hollow inner member. In some embodiments, the ultrasound scanner assembly is positioned around the second annular member.

In some embodiments, the second annular member comprises the second material, and the second annular member comprises a ring shape. In some embodiments, the support member further comprises a distal tubular member extending distally of the hollow inner member, and the second annular member and the distal tubular member comprise a flexible third material. In some embodiments, the first annular member, the sleeve member, and the second annular member form an integral component positioned around the perimeter of the hollow inner member. In some embodiments, a sidewall of the hollow inner member comprises at least one of a groove or a through-hole.

In some embodiments, the intraluminal ultrasound imaging catheter further includes: a proximal tubular member coupled to the proximal portion of the hollow inner member and extending proximally of the hollow inner member; and a distal tip member coupled to a distal portion end of the hollow inner member and extending distally of the hollow inner member, wherein the distal tip member comprises: an annular section positioned around the perimeter of the hollow inner member at a distal portion of the hollow inner member, wherein the annular section extends radially outward from the hollow inner member; and a tapered section extending distally of the annular section, wherein the proximal tubular member and the distal tip member comprise a polymer material.

According to another embodiment of the present disclosure, an intraluminal ultrasound imaging system includes: an intraluminal ultrasound imaging catheter, comprising: a flexible elongate member configured to be positioned within a body lumen of a patient; a support member coupled to a distal portion of the flexible elongate member, wherein the support member comprises: a metallic, hollow inner member comprising a first material; a polymeric ring positioned around a perimeter of the hollow inner member at a proximal portion of the hollow inner member, wherein the polymeric ring extends radially outward from the hollow inner member; and an ultrasound scanner assembly positioned around the polymeric ring of the support member, wherein the ultrasound scanner assembly is configured to obtain ultrasound imaging data of the body lumen; and a processor circuit in communication with the intraluminal ultrasound imaging catheter, wherein the processor circuit is configured to generate an intraluminal ultrasound image using the ultrasound imaging data and output the intraluminal ultrasound image to a display.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 7B is a perspective cross-sectional view of the chassis shown in FIG. 7A taken along section line 7-7, according to aspects of the present disclosure.

FIG. 11 is a cross-sectional side view of a chassis of a scanner assembly including a cylindrical hollow core including a projection extending radially outward around the perimeter of the cylindrical hollow core, and a polymer ring positioned over and around the projection, according to aspects of the present disclosure.

DETAILED DESCRIPTION

Figure 1A:
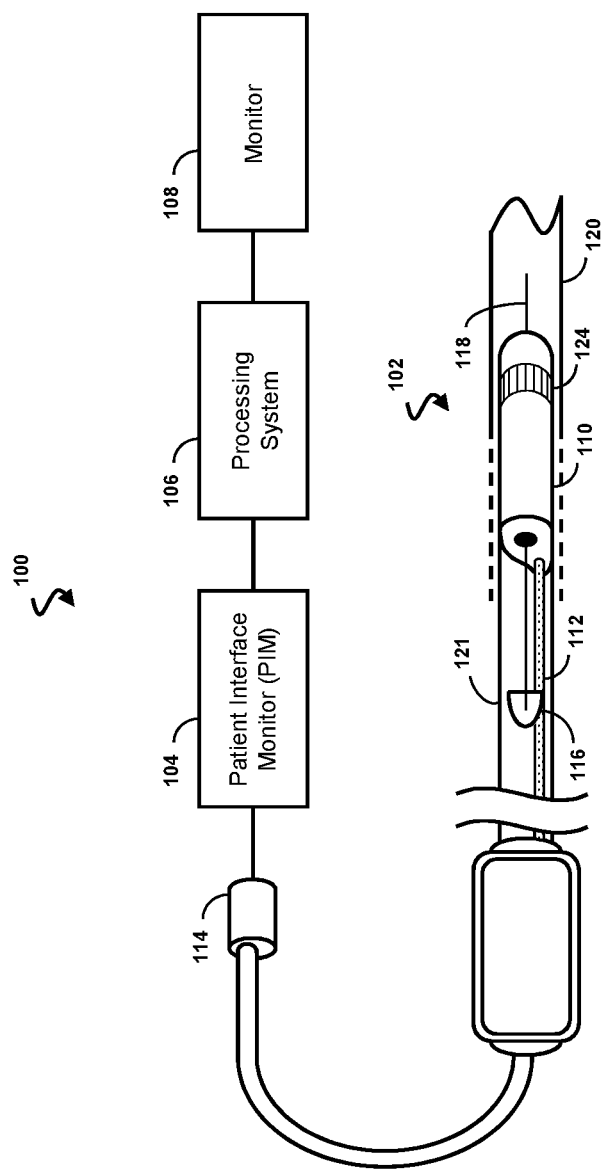
FIG. 1A is a diagrammatic schematic view of an intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1A is a diagrammatic schematic view of an ultrasound imaging system 100, according to aspects of the present disclosure. The ultrasound imaging system 100 can be an intraluminal imaging system. In some instances, the system 100 can be an intravascular ultrasound (IVUS) imaging system. The system 100 may include an intraluminal imaging device 102 such as a catheter, guide wire, or guide catheter, a patient interface module (PIM) 104, a processing system or console 106, and a monitor 108. The intraluminal imaging device 102 can be an ultrasound imaging device. In some instances, the device 102 can be IVUS imaging device, such as a solid-state IVUS device.

At a high level, the IVUS device 102 emits ultrasonic energy, or ultrasound signals, from a transducer array 124 included in scanner assembly 110 mounted near a distal end of the catheter device. The ultrasonic energy is reflected by tissue structures in the medium, such as a vessel 120, or another body lumen surrounding the scanner assembly 110, and the ultrasound echo signals are received by the transducer array 124. In that regard, the device 102 can be sized, shaped, or otherwise configured to be positioned within the body lumen of a patient. The PIM 104 transfers the received echo signals to the console or computer 106 where the ultrasound image (including the flow information) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to integrated circuit controller chip(s) 206A, 206B, illustrated in FIG. 2, included in the scanner assembly 110 to select the particular transducer array element(s), or acoustic element(s), to be used for transmit and receive, (2) providing the transmit trigger signals to the integrated circuit controller chip(s) 206A, 206B included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) 126 of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

Figure 2:
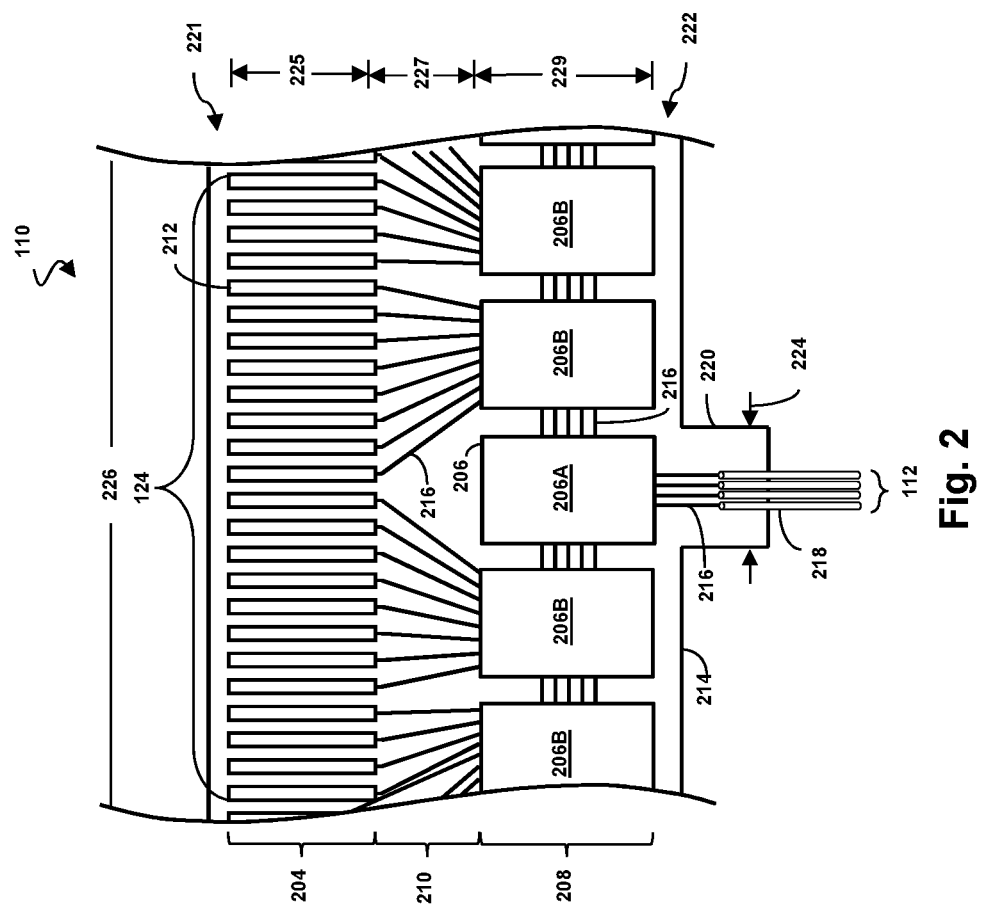
FIG. 2 is a diagrammatic view of the top of a scanner assembly in a flat configuration, according to aspects of the present disclosure.

In some embodiments, the IVUS device includes some features similar to traditional solid-state IVUS catheters, such as the EagleEye® catheter available from Koninklijke Philips N.V. and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 American Wire Gauge (AWG) wires. In an embodiment, the cable 112 can include a seven-conductor transmission line arrangement utilizing, e.g., 44 AWG wires. In some embodiments, 43 AWG wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

In an embodiment, the image processing system 106 generates flow data by processing the echo signals from the IVUS device 102 into Doppler power or velocity information. The image processing system 106 may also generate B-mode data by applying envelope detection and logarithmic compression on the conditioned echo signals. The processing system 106 can further generate images in various views, such as 2D and/or 3D views, based on the flow data or the B-mode data. The processing system 106 can also perform various analyses and/or assessments. For example, the processing system 106 can apply virtual histology (VH) techniques, for example, to analyze or assess plaques within a vessel (e.g., the vessel 120). The images can be generated to display a reconstructed color-coded tissue map of plaque composition superimposed on a cross-sectional view of the vessel.

In an embodiment, the processing system 106 can apply a blood flow detection algorithm (e.g., ChromaFlo) to determine the movement of blood flow, for example, by acquiring image data of a target region (e.g., the vessel 120) repeatedly and determining the movement of the blood flow from the image data. The blood flow detection algorithm operates based on the principle that signals measured from vascular tissue are relatively static from acquisition to acquisition, whereas signals measured from blood flow vary at a characteristic rate corresponding to the flow rate. As such, the blood flow detection algorithm may determine movements of blood flow based on variations in signals measured from the target region between repeated acquisitions. To acquire the image data repeatedly, the processing system 106 may control to the device 102 to transmit repeated pulses on the same aperture.

While the present disclosure describes embodiments related to intravascular ultrasound (IVUS) imaging using an intravascular catheter or guidewire, it is understood that one or more aspects of the present disclosure can be implemented in any suitable ultrasound imaging system, including a synthetic aperture ultrasound imaging system, a phased array ultrasound imaging system, or any other array-based ultrasound imaging system. For example, aspects of the present disclosure can be implemented in intraluminal ultrasound imaging systems using an intracardiac (ICE) echocardiography catheter and/or a transesophageal echocardiography (TEE) probe, and/or external ultrasound imaging system using an ultrasound probe configured for imaging while positioned adjacent to and/or in contact with the patient's skin. The ultrasound imaging device can be a transthoracic echocardiography (TTE) imaging device in some embodiments.

An ultrasound transducer array of ultrasound imaging device includes an array of acoustic elements configured to emit ultrasound energy and receive echoes corresponding to the emitted ultrasound energy. In some instances, the array may include any number of ultrasound transducer elements. For example, the array can include between 2 acoustic elements and 10000 acoustic elements, including values such as 2 acoustic elements, 4 acoustic elements, acoustic elements, 64 acoustic elements, 128 acoustic elements, 500 acoustic elements, 812 acoustic elements, 3000 acoustic elements, 9000 acoustic elements, and/or other values both larger and smaller. In some instances, the transducer elements of the array may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., one or more rows, one or more columns, and/or one or more orientations) can be uniformly or independently controlled and activated. The array can be configured to obtain one-dimensional, two-dimensional, and/or three-dimensional images of patient anatomy.

The ultrasound transducer elements may include piezoelectric/piezoresistive elements, piezoelectric micromachined ultrasound transducer (PMUT) elements, capacitive micromachined ultrasound transducer (CMUT) elements, and/or any other suitable type of ultrasound transducer elements. The ultrasound transducer elements of the array are in communication with (e.g., electrically coupled to) electronic circuitry. For example, the electronic circuitry can include one or more transducer control logic dies. The electronic circuitry can include one or more integrated circuits (IC), such as application specific integrated circuits (ASICs). In some embodiments, one or more of the ICs can include a microbeamformer (μBF). In other embodiments, one or more of the ICs includes a multiplexer circuit (MUX).

Figure 1B:
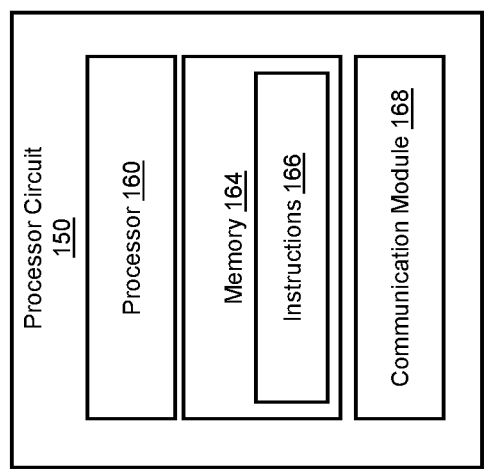
FIG. 1B is a schematic diagram of a processor circuit, according to embodiments of the present disclosure.

FIG. 1B is a schematic diagram of a processor circuit 150, according to embodiments of the present disclosure. The processor circuit 150 may be implemented in the processing system 106 and/or the imaging device 102 of FIG. 1A. As shown, the processor circuit 150 may include a processor 160, a memory 164, and a communication module 168. These elements may be in direct or indirect communication with each other, for example via one or more buses.

The processor 160 may include a central processing unit (CPU), a digital signal processor (DSP), an ASIC, a controller, a field-programmable gate array (FPGA), another hardware device, a firmware device, or any combination thereof configured to perform the operations described herein. The processor 160 may also be implemented as a combination of computing devices, e.g., a combination of a DSP and a microprocessor, a plurality of microprocessors, one or more microprocessors in conjunction with a DSP core, or any other such configuration.

The memory 164 may include a cache memory (e.g., a cache memory of the processor 160), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 164 includes a non-transitory computer-readable medium. The memory 164 may store instructions 166. The instructions 166 may include instructions that, when executed by the processor 160, cause the processor 160 to perform the operations described herein with reference to the processing system 106 and/or the imaging device 102 (FIG. 1A). Instructions 166 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 168 can include any electronic circuitry and/or logic circuitry to facilitate direct or indirect communication of data between the processor circuit 150, the imaging device 102, and/or the display 108. In that regard, the communication module 168 can be an input/output (I/O) device. In some instances, the communication module 168 facilitates direct or indirect communication between various elements of the processor circuit 150 and/or the processing system 106 (FIG. 1A).

FIG. 2 is a diagrammatic top view of a portion of a flexible assembly 200, according to aspects of the present disclosure. The flexible assembly 200 includes a transducer array 124 formed in a transducer region 204 and transducer control logic dies 206 (including dies 206A and 206B) formed in a control region 208, with a transition region 210 disposed therebetween.

The transducer control logic dies 206 are mounted on a flexible substrate 214 into which the transducers 212 have been previously integrated. The flexible substrate 214 is shown in a flat configuration in FIG. 2. Though six control logic dies 206 are shown in FIG. 2, any number of control logic dies 206 may be used. For example, one, two, three, four, five, six, seven, eight, nine, ten, or more control logic dies 206 may be used.

The flexible substrate 214, on which the transducer control logic dies 206 and the transducers 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, liquid crystal polymer, other flexible printed semiconductor substrates as well as products such as Upilex® (registered trademark of Ube Industries) and TEFLON® (registered trademark of E.I. du Pont). In the flat configuration illustrated in FIG. 2, the flexible substrate 214 has a generally rectangular shape. As shown and described herein, the flexible substrate 214 is configured to be wrapped around a support member 230 (FIG. 3) in some instances. Therefore, the thickness of the film layer of the flexible substrate 214 is generally related to the degree of curvature in the final assembled flexible assembly 110. In some embodiments, the film layer is between 5 µm and 100 µm, with some particular embodiments being between 5 µm and 25.1 µm, e.g., 6 µm.

The transducer control logic dies 206 is a non-limiting example of a control circuit. The transducer region 204 is disposed at a distal portion 221 of the flexible substrate 214. The control region 208 is disposed at a proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or, the length 227 of the transition region 210 may be less than lengths 225 and 229, the length 227 of the transition region 210 can be greater than lengths 225, 229 of the transducer region and controller region, respectively.

The control logic dies 206 are not necessarily homogenous. In some embodiments, a single controller is designated a master control logic die 206A and contains the communication interface for cable 142 which may serve as an electrical conductor, e.g., electrical conductor 112, between a processing system, e.g., processing system 106, and the flexible assembly 200. Accordingly, the master control circuit may include control logic that decodes control signals received over the cable 142, transmits control responses over the cable 142, amplifies echo signals, and/or transmits the echo signals over the cable 142. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

To electrically interconnect the control logic dies 206 and the transducers 212, in an embodiment, the flexible substrate 214 includes conductive traces 216 formed in the film layer that carry signals between the control logic dies 206 and the transducers 212. In particular, the conductive traces 216 providing communication between the control logic dies 206 and the transducers 212 extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 142 when the conductors 218 of the cable 142 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 1-5 µm. For example, in an embodiment, 5 µm conductive traces 216 are separated by 5 µm of space. The width of a conductive trace 216 on the flexible substrate may be further determined by the width of the conductor 218 to be coupled to the trace/pad.

The flexible substrate 214 can include a conductor interface 220 in some embodiments. The conductor interface 220 can be a location of the flexible substrate 214 where the conductors 218 of the cable 142 are coupled to the flexible substrate 214. For example, the bare conductors of the cable 142 are electrically coupled to the flexible substrate 214 at the conductor interface 220. The conductor interface 220 can be tab extending from the main body of flexible substrate 214. In that regard, the main body of the flexible substrate 214 can refer collectively to the transducer region 204, controller region 208, and the transition region 210. In the illustrated embodiment, the conductor interface 220 extends from the proximal portion 222 of the flexible substrate 214. In other embodiments, the conductor interface 220 is positioned at other parts of the flexible substrate 214, such as the distal portion 221, or the flexible substrate 214 may lack the conductor interface 220. A value of a dimension of the tab or conductor interface 220, such as a width 224, can be less than the value of a dimension of the main body of the flexible substrate 214, such as a width 226. In some embodiments, the substrate forming the conductor interface 220 is made of the same material(s) and/or is similarly flexible as the flexible substrate 214. In other embodiments, the conductor interface 220 is made of different materials and/or is comparatively more rigid than the flexible substrate 214. For example, the conductor interface 220 can be made of a plastic, thermoplastic, polymer, hard polymer, etc., including polyoxymethylene (e.g., DELRIN®), polyether ether ketone (PEEK), nylon, Liquid Crystal Polymer (LCP), and/or other suitable materials.

Figure 3:
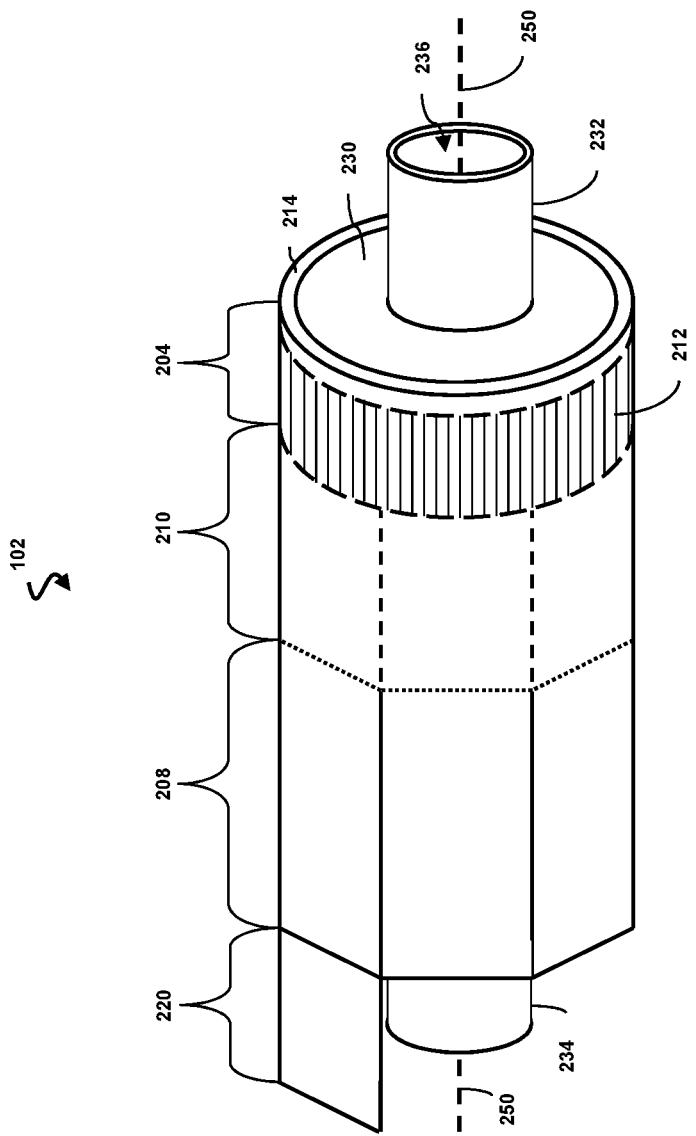
FIG. 3 is a diagrammatic perspective view of the scanner assembly shown in FIG. 2 in a rolled configuration around a support member, according to aspects of the present disclosure.

FIG. 3 illustrates a perspective view of the device 102 with the scanner assembly 110 in a rolled configuration. In some instances, the assembly 110 is transitioned from a flat configuration (FIG. 2) to a rolled or more cylindrical configuration (FIG. 3). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND SENSING ASSEMBLY HAVING A FLEXIBLE SUBSTRATE," each of which is hereby incorporated by reference in its entirety.

In some embodiments, the transducer elements 212 and/or the controllers 206 can be positioned in in an annular configuration, such as a circular configuration or in a polygon configuration, around a longitudinal axis 250 of a support member 230. It will be understood that the support member 230 may comprise, or be referred to as, a chassis. It will also be understood that the longitudinal axis 250 of the support member 230 may also be referred to as the longitudinal axis of the scanner assembly 110, the flexible elongate member 121, and/or the device 102. For example, a cross-sectional profile of the imaging assembly 110 at the transducer elements 212 and/or the controllers 206 can be a circle or a polygon. Any suitable annular polygon shape can be implemented, such as a based on the number of controllers/transducers, flexibility of the controllers/transducers, etc., including a pentagon, hexagon, heptagon, octagon, nonagon, decagon, etc. In some examples, the plurality of transducer controllers 206 may be used for controlling the plurality of ultrasound transducer elements 212 to obtain imaging data associated with the vessel 120.

The support member 230 can be referenced as a unibody or chassis in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, ('220 application) the entirety of which is hereby incorporated by reference herein. The support member 230 can be a ferrule having a distal flange or portion 232 and a proximal flange or portion 234. The support member 230 can be tubular in shape and define a lumen 236 extending longitudinally therethrough. The lumen 236 can be sized and shaped to receive the guide wire 118. The support member 230 can be manufactured using any suitable process. For example, the support member 230 can be machined and/or electrochemically machined or laser milled, such as by removing material from a blank to shape the support member 230, or molded, such as by an injection molding process.

Figure 4:
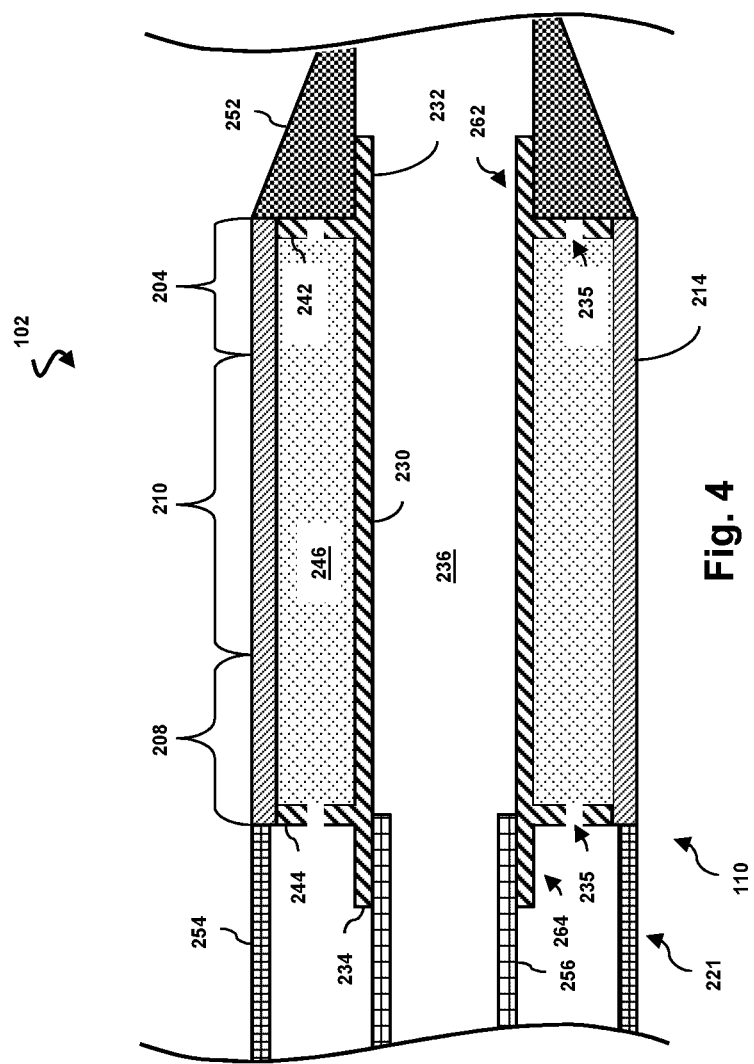
FIG. 4 is a diagrammatic cross-sectional side view of a scanner assembly in a rolled configuration around a support member, according to aspects of the present disclosure.

Referring now to FIG. 4, shown there is a diagrammatic cross-sectional side view of a distal portion of the intraluminal imaging device 102, including the flexible substrate 214 and the support member 230, according to aspects of the present disclosure. The support member 230 can be referenced as a unibody or chassis in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The support member 230 can be ferrule having a distal portion 262 and a proximal portion 264. The support member 230 can define a lumen 236 extending along the longitudinal axis LA. The lumen 236 is in communication with the entry/exit port 116 and is sized and shaped to receive the guide wire 118 (FIG. 1A). The support member 230 can be manufactured according to any suitable process. For example, the support member 230 can be machined and/or electrochemically machined or laser milled, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and stands 242, 244, that are fixedly coupled to one another. In some cases, the support member 230 and/or one or more components thereof may be completely integrated with inner member 256. In some cases, the inner member 256 and the support member 230 may be joined as one, e.g., in the case of a polymer support member.

Stands 242, 244 that extend vertically are provided at the distal and proximal portions 262, 264, respectively, of the support member 230. The stands 242, 244 elevate and support the distal and proximal portions of the flexible substrate 214. In that regard, portions of the flexible substrate 214, such as the transducer portion or region 204, can be spaced from a central body portion of the support member 230 extending between the stands 242, 244. The stands 242, 244 can have the same outer diameter or different outer diameters. For example, the distal stand 242 can have a larger or smaller outer diameter than the proximal stand 244 and can also have special features for rotational alignment as well as control chip placement and connection. To improve acoustic performance, any cavities between the flexible substrate 214 and the surface of the support member 230 are filled with a backing material 246. The liquid backing material 246 can be introduced between the flexible substrate 214 and the support member 230 via passageways 235 in the stands 242, 244. In some embodiments, suction can be applied via the passageways 235 of one of the stands 242, 244, while the liquid backing material 246 is fed between the flexible substrate 214 and the support member 230 via the passageways 235 of the other of the stands 242, 244. The backing material can be cured to allow it to solidify and set. In various embodiments, the support member 230 includes more than two stands 242, 244, only one of the stands 242, 244, or neither of the stands. In that regard the support member 230 can have an increased diameter distal portion 262 and/or increased diameter proximal portion 264 that is sized and shaped to elevate and support the distal and/or proximal portions of the flexible substrate 214.

The support member 230 can be substantially cylindrical in some embodiments. Other shapes of the support member 230 are also contemplated including geometrical, non-geometrical, symmetrical, non-symmetrical, cross-sectional profiles. As the term is used herein, the shape of the support member 230 may reference a cross-sectional profile of the support member 230. Different portions the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can include a flexible elongate member. The proximal inner member 256 can be received within a proximal flange 234. The proximal outer member 254 abuts and is in contact with the flexible substrate 214. A distal member 252 is coupled to the distal portion 262 of the support member 230. For example, the distal member 252 is positioned around the distal flange 232. The distal member 252 can abut and be in contact with the flexible substrate 214 and the stand 242. The distal member 252 can be the distal-most component of the intraluminal imaging device 102.

One or more adhesives can be disposed between various components at the distal portion of the intraluminal imaging device 102. For example, one or more of the flexible substrate 214, the support member 230, the distal member 252, the proximal inner member 256, and/or the proximal outer member 254 can be coupled to one another via an adhesive. The assembly 110 shown in FIG. 2 can be activated according to a pulse sequence or scan sequence to form coherent beams of ultrasound energy to generate an image.

As noted above, conventional IVUS imaging devices may include a support member or chassis, also referred as unibody or housing, that is formed of a metal tube and provides structural support, rigidity, radiopacity and other characteristics to the IVUS device. Conventional chassis suffer from a number of drawbacks. For example, the manufacturing techniques available for metals (e.g., milling, welding, etc.) limit the types of chassis and mechanical features that can be produced. Similarly, some metals cannot be re-flowed with polymers and/or do not effectively scatter or attenuate ultrasound waves. The present disclosure describes exemplary embodiments of a chassis formed of multiple materials that incorporates various mechanical and/or acoustic properties for improved performance of the IVUS device. In particular, the materials and constructions of the chassis described herein are selected to enhance or improve properties and characteristics such as strength, flexibility, maneuverability, resilience, acoustic performance, machineability, and/or radiopacity. It will be understood that, although the embodiments discussed below are described with respect to IVUS imaging catheters, it will be understood that the embodiments may be used with any suitable device configured to be inserted into a body lumen of a patient.

FIGS. 5-11 provide various structural arrangements and embodiments of a multi-material support member or chassis used in an IVUS imaging catheter, according to aspects of the present disclosure. The chassis include a hollow inner member formed of a first material, and one or more structures (e.g., rings, sleeves, flexible components) formed of one or more different materials. It will be understood that the support members or chassis described below may be used with a scanner assembly, such as the scanner assembly 110 shown in FIG. 1A. In some aspects, the scanner assembly may comprise, or be referred to as an ultrasound transducer array, a flex circuit, an ultrasound transducer, acoustic assembly, and or an integrated circuit coupled to a substrate. A scanner assembly may be positioned around a perimeter of a chassis, and coupled to other components of a catheter, including a flexible inner member, a flexible outer member, and/or a flexible tip member.

Figure 5A:
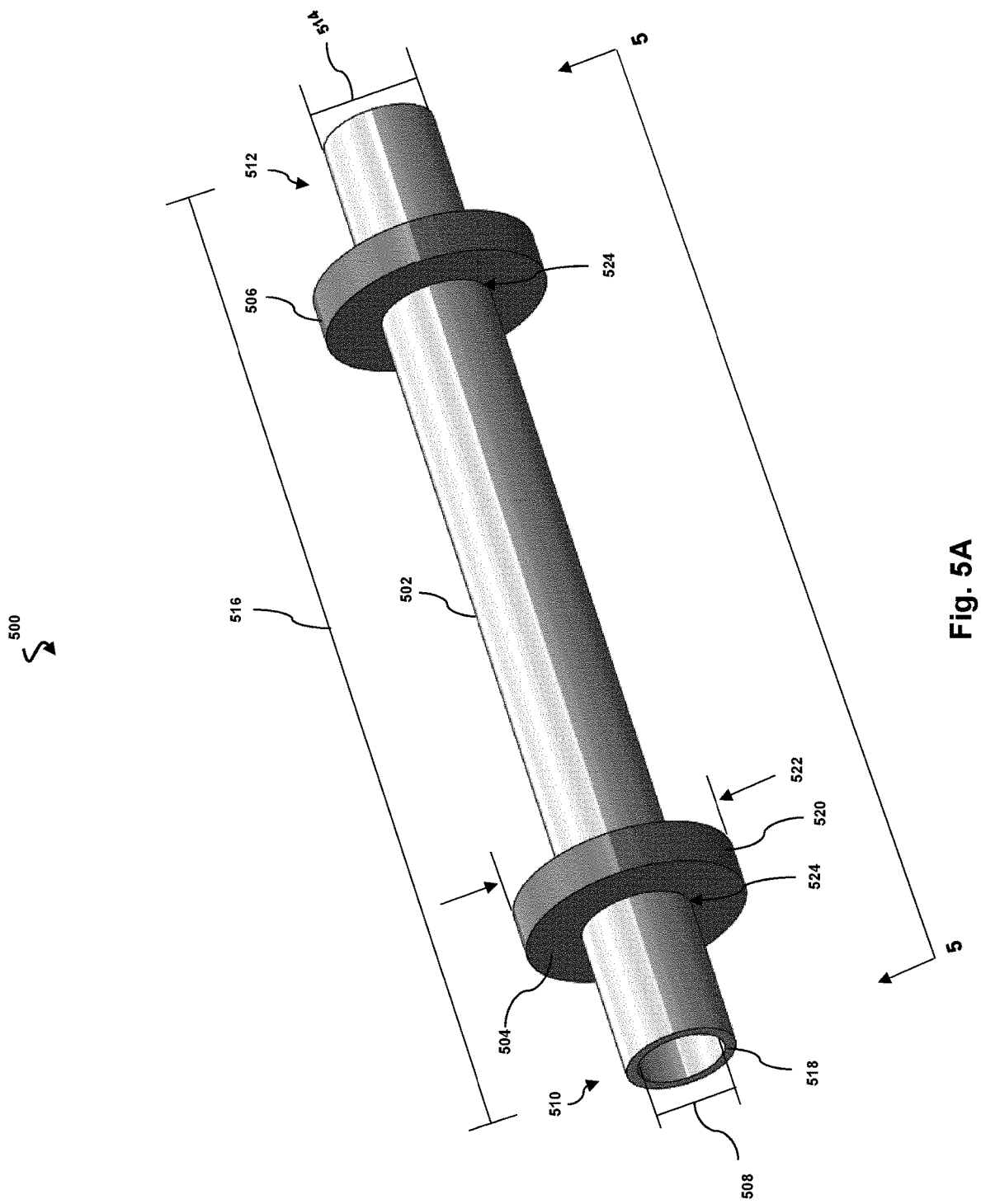
FIG. 5A is perspective view of a chassis of a scanner assembly including a cylindrical hollow core with two polymeric rings attached around its perimeter, according to aspects of the present disclosure.
Figure 5B:
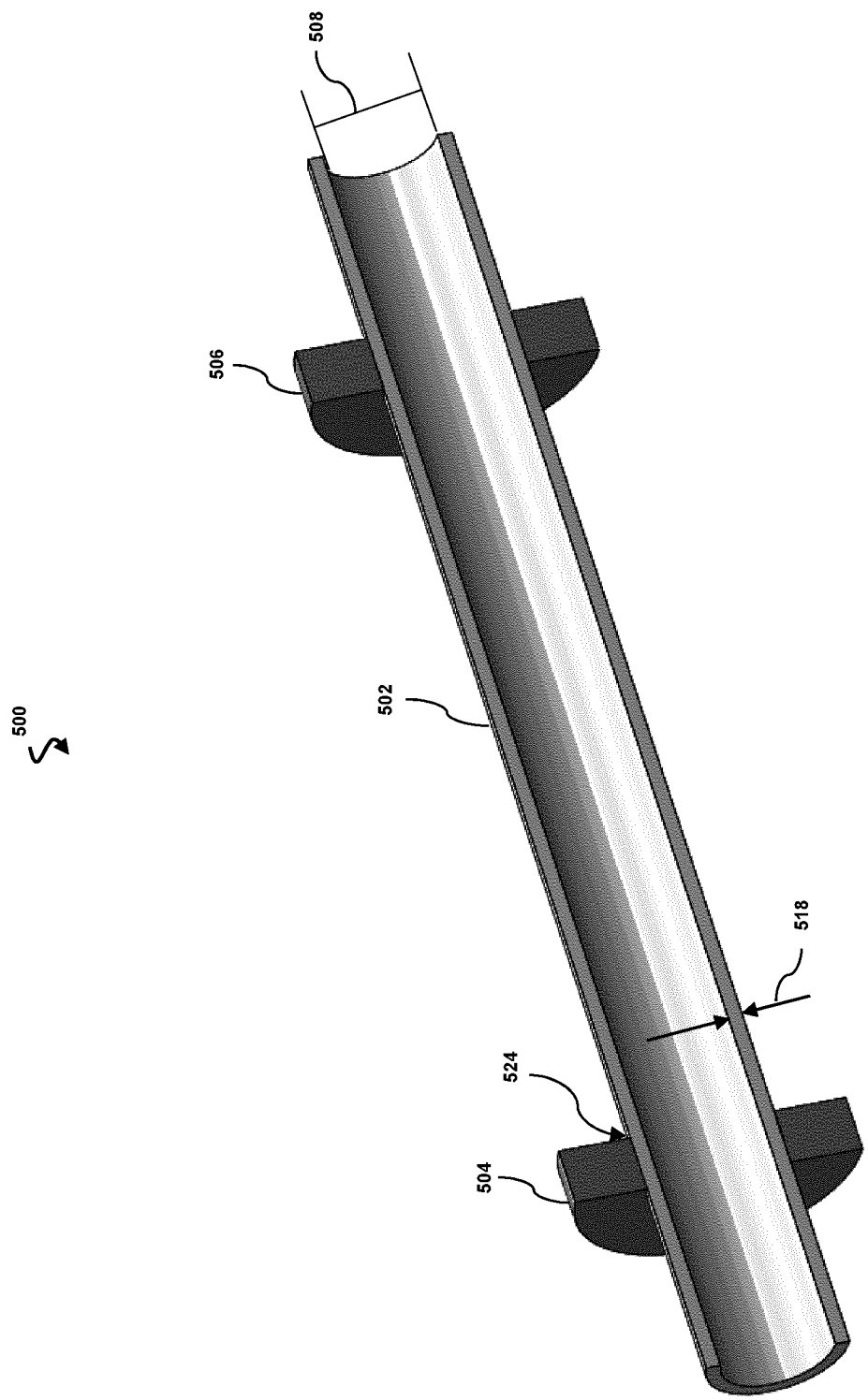
FIG. 5B is a perspective cross-sectional view of the chassis shown in FIG. 5A, taken along section line 5-5, according to aspects of the present disclosure.

FIG. 5A is perspective view of a chassis 500 configured to be used with a scanner assembly (e.g., scanner assembly 110, FIGS. 1A, 2), the chassis 500 including a hollow cylindrical member 502 with two polymeric rings 504, 506 attached around a perimeter of the hollow cylindrical member 502. FIG. 5B is a perspective cross-sectional side view of the chassis 500 shown in FIG. 5A taken along section line 5-5. In an exemplary embodiment, the hollow cylindrical member 502, which may also be referred to as a hollow inner member, a cylindrical core member, a core, a metal core, or tube, may comprise, is formed of a metallic material. However, in other embodiments, the hollow cylindrical member 502 may comprise a polymer, ceramic, or other type of material. The two rings 504, 506 may be referred to as annular members, in some aspects. In the illustrated embodiment, the two rings 504, 506, or annular members, comprise circular shapes. In other embodiments, the annular members 504, 506, comprise polygonal shapes, elliptical shapes, and/or combinations thereof. For example, in some embodiments, the annular members 504, 506 comprise rectangular, hexagonal, octogonal, nonogonal, and/or any other suitable shapes. The two rings 504, 506 may comprise, or may be formed of, a polymer-based material. In an exemplary embodiment, the metallic material of the cylindrical member 502, or hollow core, comprises stainless-steel. However, other metallic materials may be used as well, including radiopaque materials such as platinum and iridium, tungsten, aluminum, and/or nitinol.

The hollow core 502 may provide structural support and/or protection for electrical components and sensitive materials on the scanner assembly. The hollow core 502 may comprise a cylindrical and/or annular cross-sectional shape. In some aspects, the hollow core 502 shown in FIGS. 5A and 5B comprises a generally cylindrical shape. The generally cylindrical shape may be continuous, or may include grooves, through holes, or other features. Although the hollow core 502 comprises a cylindrical shape in FIG. 5A, the hollow core 502 may include other profiles or shapes, such as a polygon, rectangle, triangle, ellipse, and/or combinations thereof. In the illustrated embodiment, the hollow core 502 includes a uniform shape and uniform inner and outer diameters from the proximal end 510 to the distal end 512. However, in some embodiments, the hollow core 502 comprises one or more non-uniform diameters, profiles, shapes, thicknesses, surfaces, or other features from the proximal end 510 to the distal end 512. The hollow core 502 may comprise a section or length of an extruded tube, in some embodiments.

In the illustrated embodiment, the hollow core 502 has dimensions including inner diameter 508, which may range between 0.0217-0.0227 inches, outer diameter 514, which may range between 0.0247-0.0257 inches, thickness 518, which may range between 0.0027-0.0037 inches, and length 516, which may range between 0.234-0.271 inches. It will be understood that the ranges of the dimensions listed above are exemplary and may comprise other values, both larger and smaller than those listed. The two polymeric rings 504, 506 are attached around the perimeter of the hollow core 502. The polymeric rings 504, 506 comprise structures of a material different from the material of the core 502, and protrude radially outward from a perimeter of the core 502. Each polymeric ring 504 and 506 includes a cylindrical, ring, and/or annular shape. In some aspects, the rings 504, 506 may be described as washers. However, in other embodiments, one or both of the polymeric rings 504, 506 may comprise other shapes or profiles, including polygons, such as octagons, nonagons, rectangles, triangles, or any combination thereof. Each polymeric ring 504 and 506 has dimensions including an inner diameter 514, which may range between 0.018-0.030 inches, an outer diameter 522, which may range between 0.030-0.050 inches, and a width 520, which may range between 0.002-0.030 inches. In some aspects, the dimensions and values provided herein may be suitable for a catheter that accommodates a guidewire of up to 0.014 inches. However, it will be understood that these values are only exemplary and are not intended to limit the scope of the present disclosure. For example, the dimensions provided herein could be modified to accommodate guidewires or intraluminal devices of other sizes. For example, in some embodiments, the dimensions and values provided herein could be modified to accommodate a guidewire of up to 0.035 inches. In some embodiments, the support member is configured for applications without the use of a guidewire. Still other ranges are contemplated. For example, one or more of the exemplary dimensions provided above could be increased or decreased according to different diagnostic applications. For example, one or more of the dimensions (e.g., the upper bound and/or the lower bound) provided above could be modified by 0.5×, 1.5×, 2×, 3×, 5×, or any other suitable multiplier. In various embodiments, the intraluminal device can be used in coronary vasculature, peripheral vasculature, intracardiac applications, endoscopic applications, etc. The values of the noted and/or other dimensions of the intraluminal device can be selected according to the relatively larger or smaller dimensions of the body lumen in which the intraluminal device is to be positioned.

The material of each polymeric ring 504, 506 may include a polymer-based material, a polymer-based composite, a polymer-based material reinforced with metal components or coatings, and/or any combination thereof. The material of each polymeric ring 504, 506 may include conductive, radiopaque, and/or acoustic properties. The polymeric rings 504, 506 provide support for the scanner assembly as it is wrapped into a cylindrical shape. The polymeric rings 504, 506 may be attached onto the hollow core 502 by overmolding, by interference fit, adhesives, or any other suitable form of attachment. In one embodiment, the polymeric rings 504, 506 are formed by extruding a tubing, cutting a length of the tubing, and sliding the cut portion of the tubing over the hollow core 502. The two polymeric rings 504, 506 may be secured onto the hollow core 502 by addition of adhesive at the ring-cylinder interface 524. The adhesive can include polymer, metal, composite based material, or any combination thereof. The hollow core 502 as well as the polymeric rings 504, 506 may include patterned surfaces with various geometric features and sizes to improve the attachment of the rings 504, 506 to the hollow core 502.

Figure 6A:
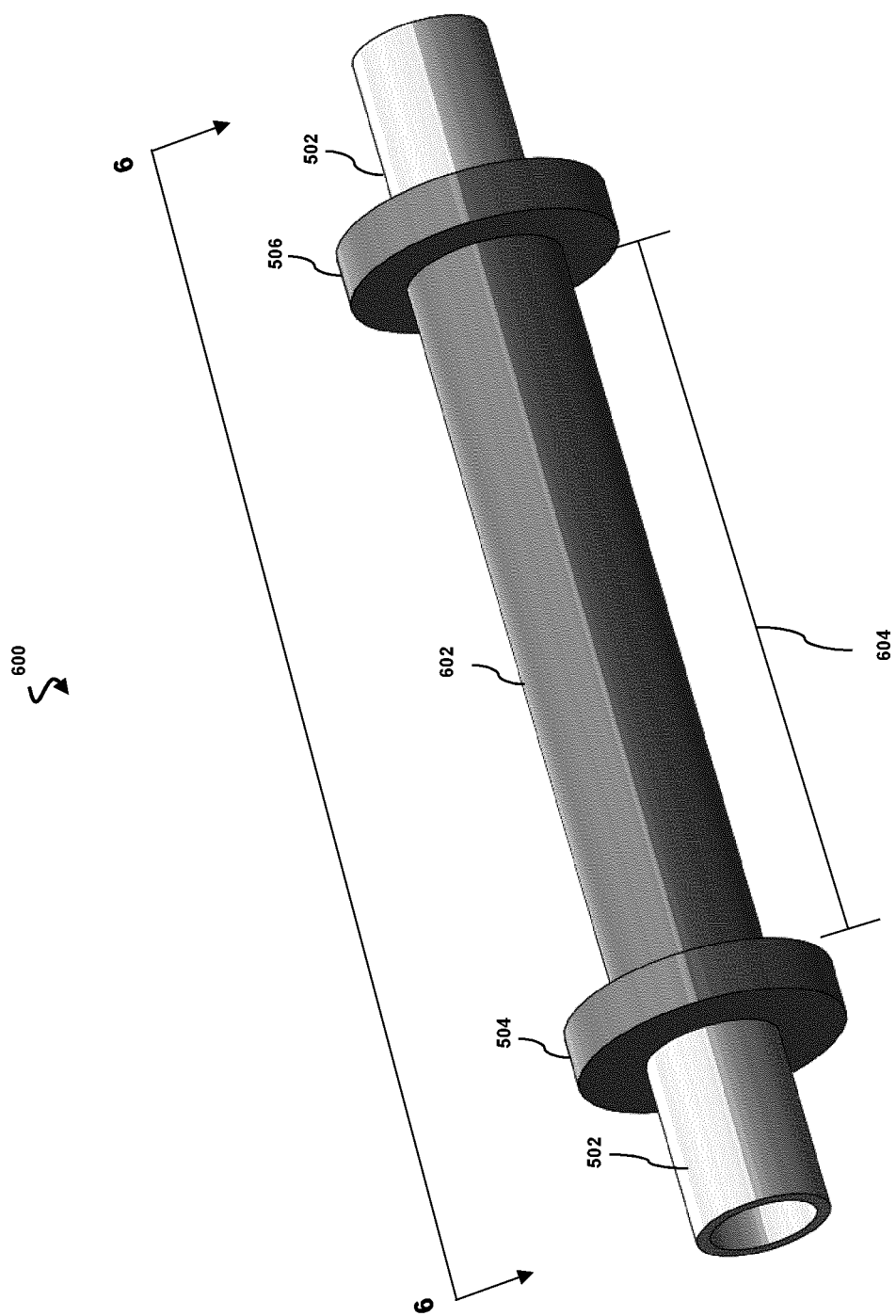
FIG. 6A is perspective view of a chassis of a scanner assembly including a cylindrical hollow core with two polymeric rings and a polymeric inner member attached around the perimeter of the hollow core, according to aspects of the present disclosure.
Figure 6B:
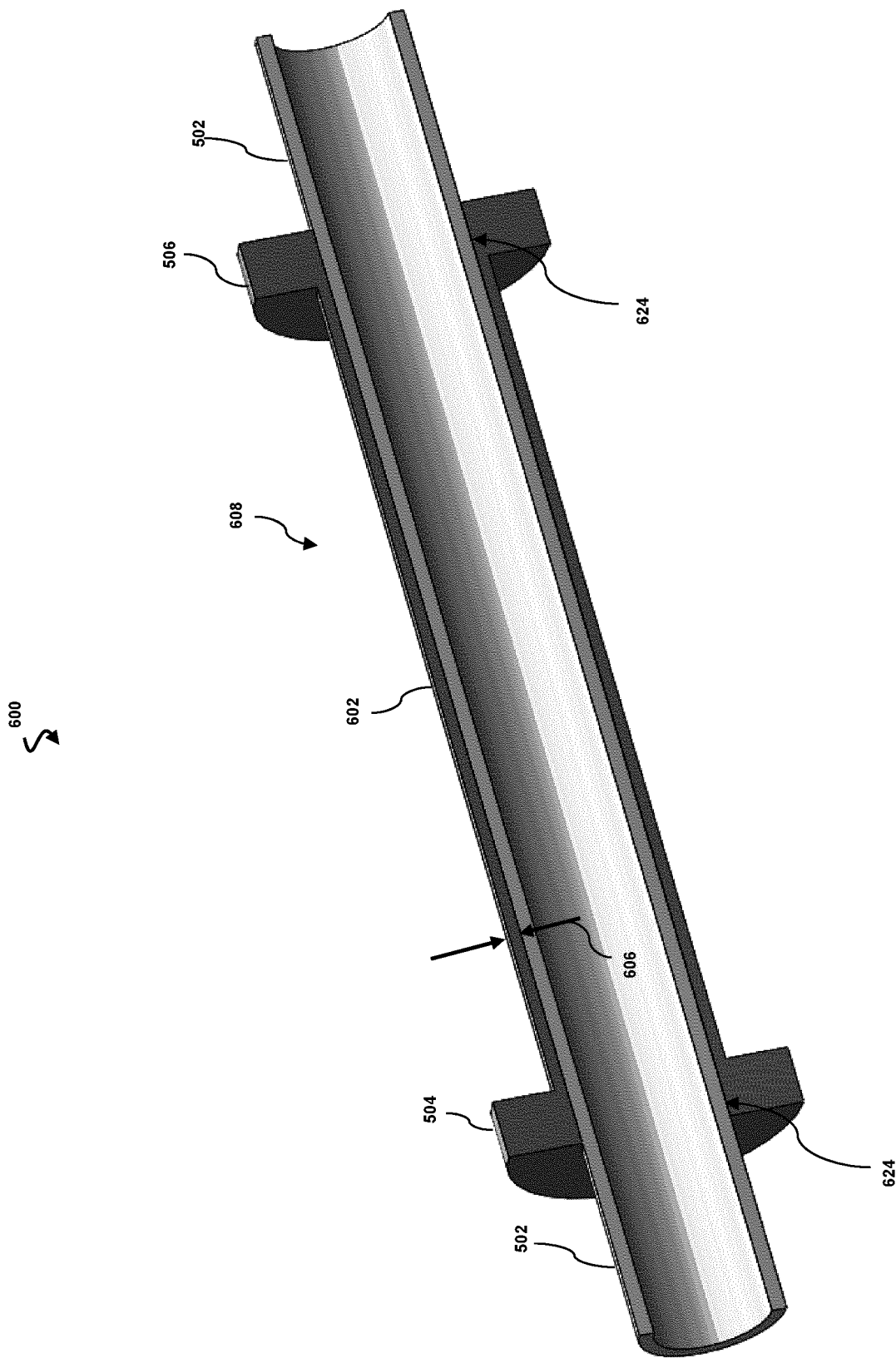
FIG. 6B is a perspective cross-sectional view of the chassis shown in FIG. 6A, taken along section line 6-6, according to aspects of the present disclosure.

FIG. 6A is perspective view of a chassis 600 of a scanner assembly, according to one embodiment of the present disclosure. In some aspects, the chassis 600 includes features similar or identical to the chassis 500 of FIGS. 5A and 5B, including a cylindrical hollow core 502 with two polymeric rings 504, 506 positioned around a perimeter of the hollow core 502. Referring to FIGS. 6A and 6B, the chassis 600 further includes a polymeric inner member 602 positioned between the polymeric rings 504, 506 and attached around the perimeter of the hollow core 502. In some aspects, the polymeric inner member 602 may be referred to as a sleeve member, or a sheath. FIG. 6B is a perspective cross-sectional side view of the chassis 600 shown in FIG. 6A taken along section line 6-6. The chassis 600 includes the cylindrical hollow core 502 with two polymeric rings 504, 506. In some aspects, the hollow core 502 and/or polymeric rings 504, 506 may comprise dimensions similar or identical to the chassis 500 shown in FIGS. 5A and 5B. In the embodiment shown in FIGS. 6A and 6B, the chassis 600 further comprises an inner member 602 formed between the two polymeric rings 504, 506, as illustrated in FIG. 6A. The inner member 602 has length 604, which may range between 9-10 inches, and thickness 606, which may range between 0.0045-0.006 inches. The chassis 600 also includes a diameter, which may be similar or equal to that of the outer diameter 514 of chassis 500. In the illustrated embodiment, the inner member 602 is formed as one integral assembly 608 with the two-polymeric rings 504, 506, which is over molded onto the cylindrical hollow core 502. The inner member comprises a material that may be the same as the material of the polymeric rings 504, 506, or may comprise a different material. The integral assembly 608 forms an attachment or interface 624 with the cylindrical hollow core 502. In some embodiments, the integral assembly 608 is formed my injection molding. In other embodiments, the integral assembly 608 is formed by extruding a tubing, cutting to length, machining to form rings 504, 506, and positioning the integral assembly 608 over the hollow core 502. The integral assembly 608 may be coupled to the hollow core 502 using an interference fit, an adhesive, and/or any other suitable form of attachment. The adhesive may include polymeric, metallic, and/or composite based materials. In other embodiments, the inner member 602 may be formed as separate member from the rings 504, 506, forming an independent attachment or interface with the hollow core 502. In some embodiments, the inner member 602 and/or integral assembly 608 includes a patterned inner and/or outer surface with various geometric features and sizes. The inclusion of the inner member 602 over the hollow core 502 may facilitate easier attachment and controlled spacing between multiple features (e.g., polymer rings 504, 506) onto to the chassis 600. Although the inner member 602, which may also be referred to as a sleeve member, comprises a circular or cylindrical shape in the illustrated embodiment, the inner member 602 may comprise other shapes or profiles, including polygonal, elliptical, and/or combinations thereof.

Figure 7A:
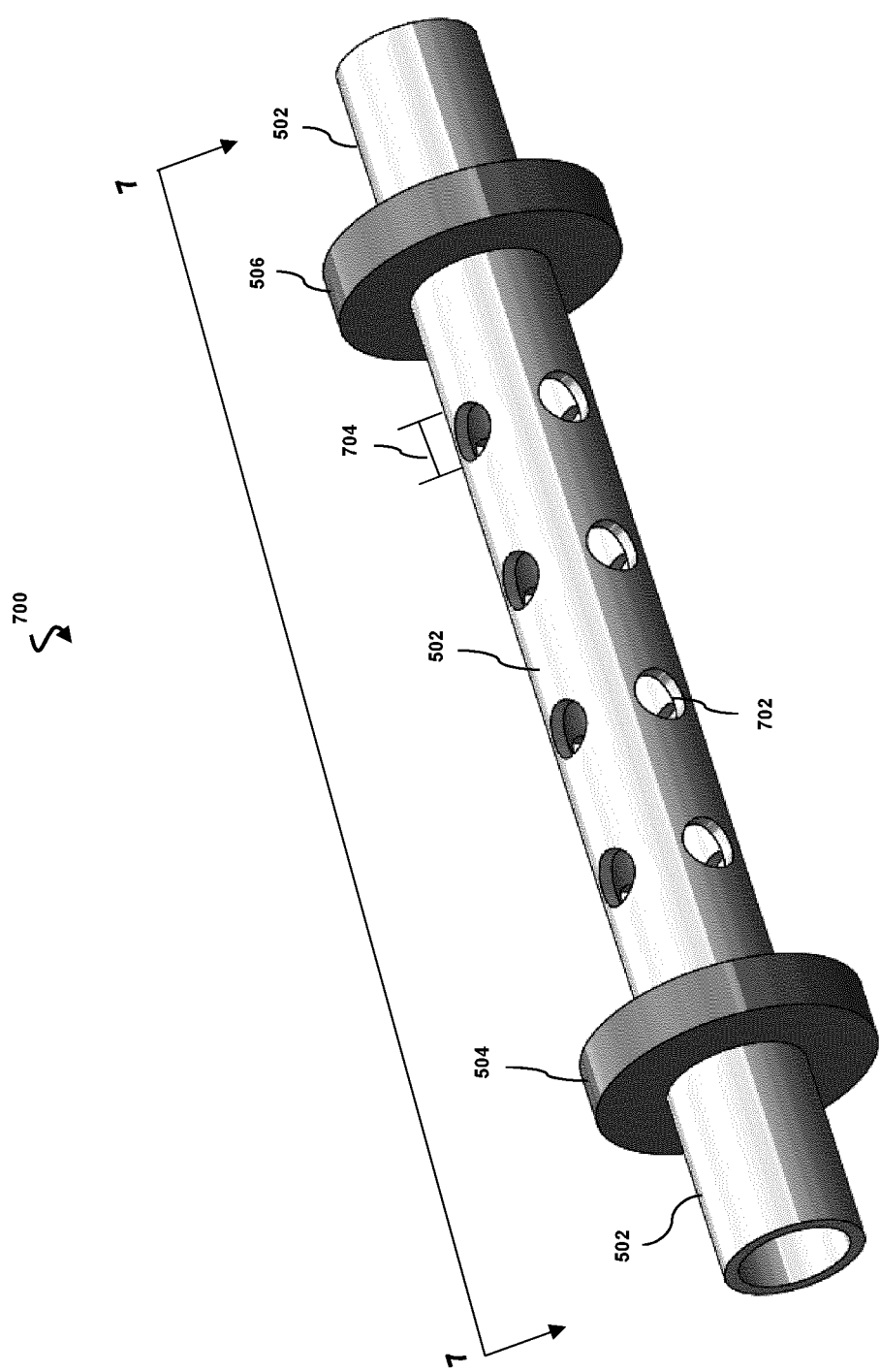
FIG. 7A is perspective view of a chassis of a scanner assembly including a cylindrical hollow core with through-holes and two polymeric rings attached around the perimeter of the hollow core, according to aspects of the present disclosure.

FIG. 7A is perspective view of a chassis 700 of a scanner assembly including cylindrical hollow core 502 with two polymeric rings 504, 506 and inner pass-through holes 702 disposed around a perimeter of the hollow core. FIG. 7B is a perspective cross-sectional side view of the chassis 700 shown in FIG. 7A taken along section line 7-7. The chassis 700 may include features similar or identical to the chassis 500 shown in FIG. 5. Referring to FIGS. 7A and 7B, the chassis 700 includes a cylindrical hollow core 502 with two polymeric rings 504, 506 positioned around the perimeter of the hollow core 502. The chassis 700 may include dimensions similar or identical to the chassis 500 shown in FIGS. 5A and 5B. The chassis 700 shown in FIGS. 7A and 7B further includes pass-through holes or grooves 702 disposed around the perimeter of the cylindrical hollow core 502. The cylindrical hollow core 502 may include one, two, three, four, five, ten, fifteen, twenty, or any other suitable number of pass-through holes 702, both greater and smaller. Each pass-through hole 702 includes a diameter 704. In some embodiments, the diameters of each of the pass-through holes 702 are the same. In other embodiments, the diameter of at least one of the pass-through holes 702 differs from the diameter of another pass-through hole 702. The presence of the pass-through holes 702 around the perimeter of the cylindrical hollow core 502 may serve as a mechanical interference point to aid with positioning and adhesion of other materials attached to the chassis 700. In some embodiments, the chassis 700 includes grooves instead of holes, such that the grooves do not extend completely through the sidewall of the hollow core 502.

Further, referring to FIG. 7B, the hollow core 502 includes recesses 706 extending inward from the outer surface of the hollow core 502, at least partially around the perimeter of the hollow core 502. In some aspects, inclusion of the recesses 706 on the outer surface of the cylindrical hollow core 502 may facilitate improved attachment or coupling of the polymer rings 504, 506 onto the cylindrical hollow core 502. For example, the recesses 706 may improve bonding of the polymer rings 504, 506 to the hollow core 502, and/or retain the polymer rings 504, 506 at their respective longitudinal positions on the hollow core 502. As described above, in some embodiments, the polymer rings 504, 506 are over molded onto the hollow core 502 such that the polymer material of the rings 504, 506 at least partially fills the recesses 706.

Figure 8A:
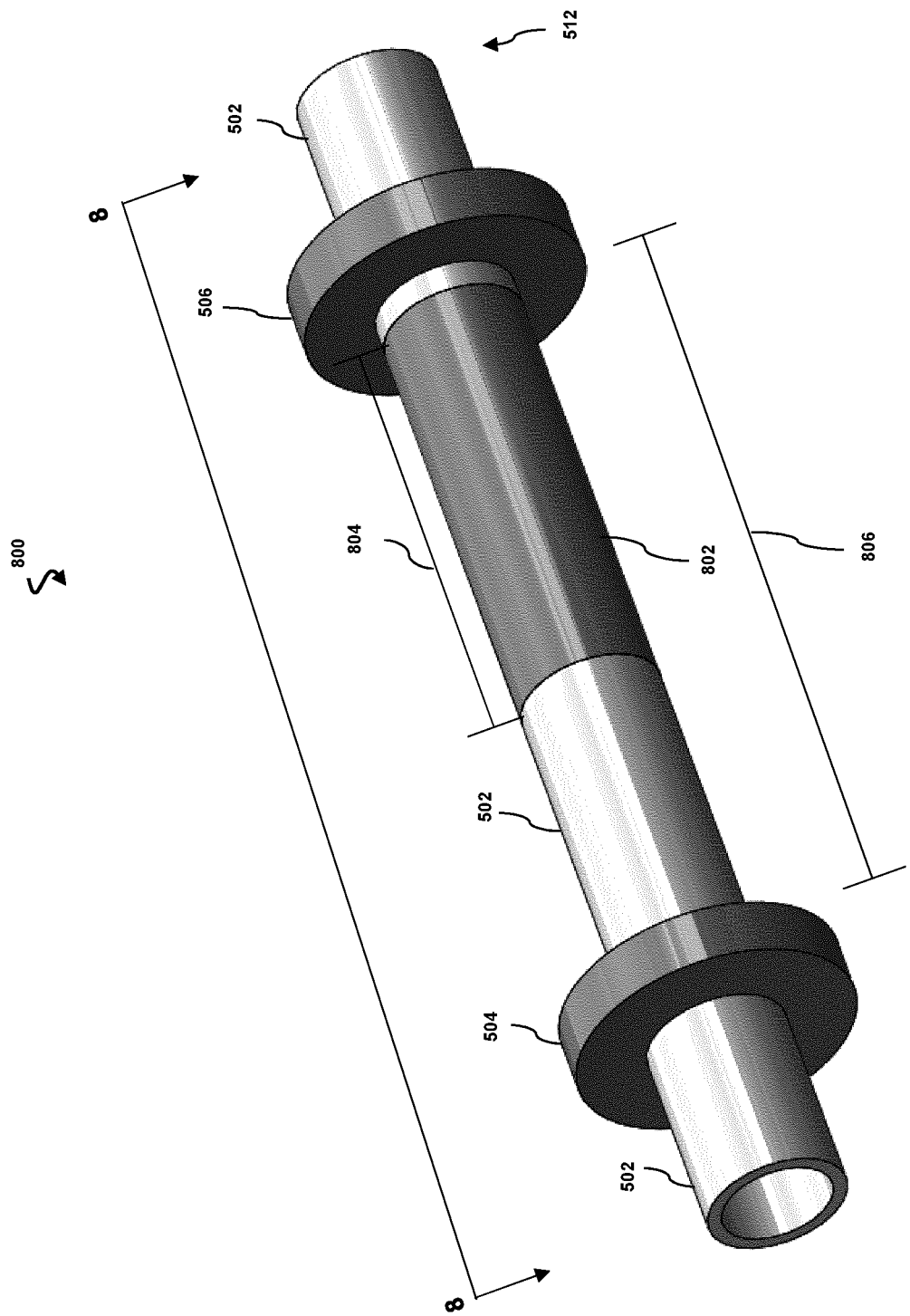
FIG. 8A is perspective view of a chassis of a scanner assembly including a cylindrical hollow core with two polymeric rings and an inner member attached around its perimeter, according to aspects of the present disclosure.
Figure 8B:
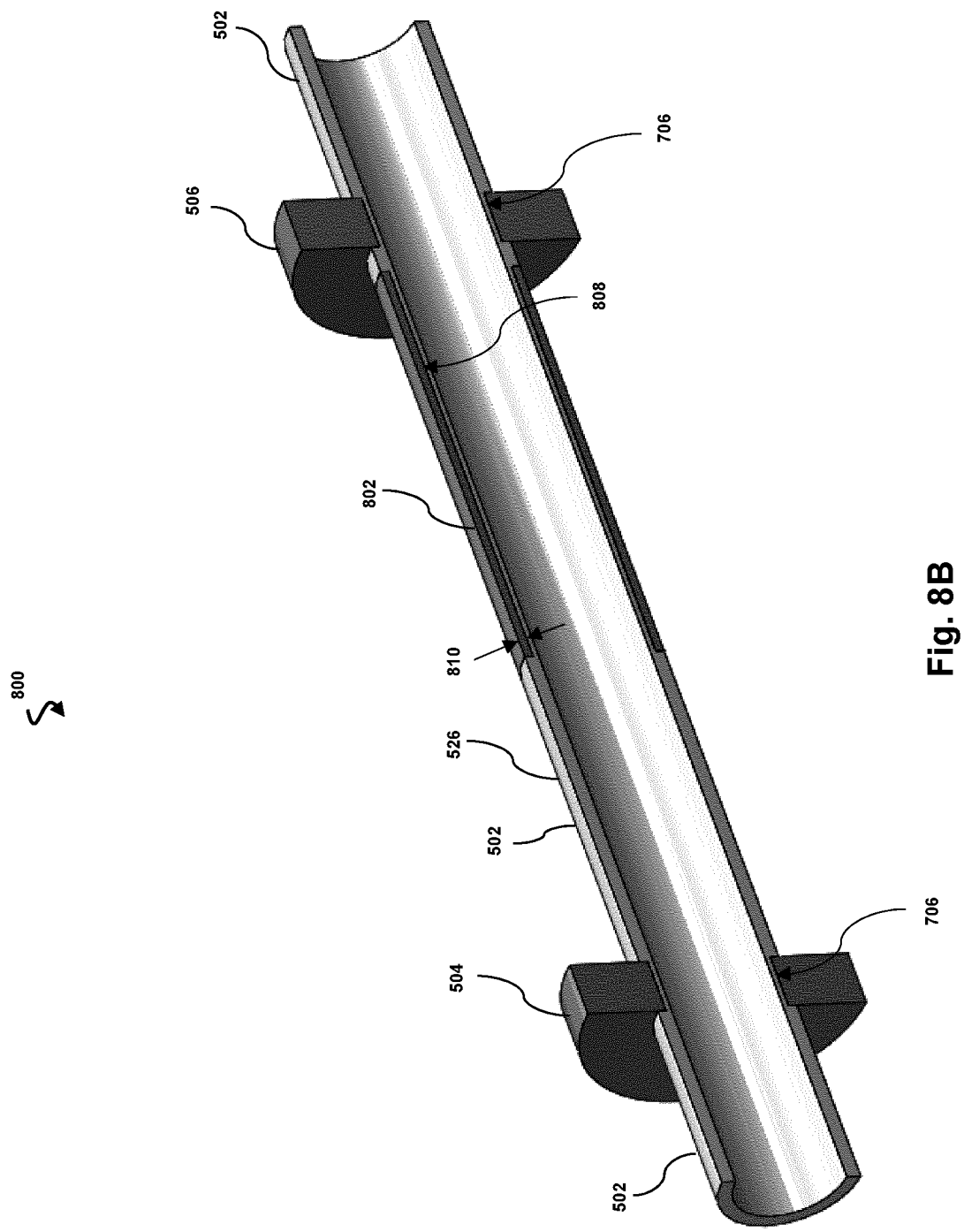
FIG. 8B is a perspective cross-sectional side view of the chassis shown in FIG. 8A taken along section line 8-8, according to aspects of the present disclosure.
Figure 8C:
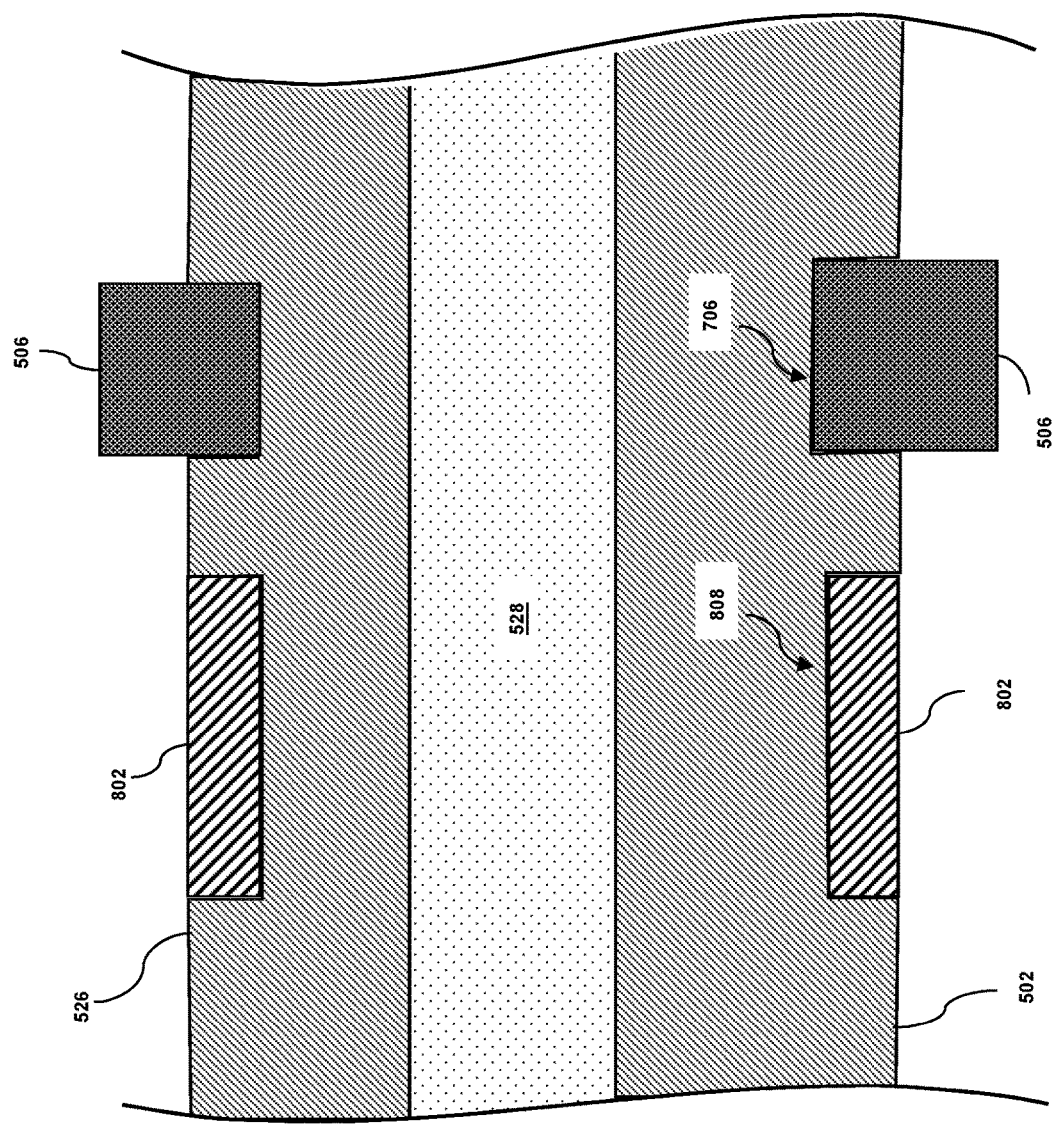
FIG. 8C is a magnified diagrammatic cross-sectional view of the chassis shown in FIG. 9A along section line 8-8, according to aspects of the present disclosure.

FIG. 8A is perspective view of a chassis 800 of a scanner assembly, including a cylindrical hollow core 502 with two polymeric rings 504, 506, and an acoustic member 802, which may also be referred to as a sleeve member or inner member, positioned around a middle or intermediate portion of the core 502, extending at least partially around its perimeter. The intermediate portion or section is positioned between the distal and proximal portions or sections of the hollow core 502. FIG. 8B is a perspective cross-sectional side view of the chassis 800 shown in FIG. 8A taken along section line 8-8. FIG. 8C is a magnified, diagrammatic cross-sectional view of the chassis 800 shown in FIG. 8A taken along line 8-8, showing recesses 706 and 808. The chassis 800 can include some features and dimensions similar or identical to the chassis 500 shown in FIGS. 5A and 5B, including the hollow core 502 and polymer rings 504, 506. The chassis 800 shown in FIGS. 8A-8C is formed with an inner member 802 disposed between the two polymeric rings 504, 506. In the illustrated embodiment, the length 804 of the inner member 802 extends approximately from a center of the cylindrical hollow core 502 to a location proximate the polymeric ring 506. The inner member 802 can be positioned over an outer surface of the cylindrical hollow core 502 by over molding, coating, doping, or positioning a sleeve over the hollow core 502. For example, in some embodiments, the hollow core 502 is placed into a mold and the inner member 802 is molded over the outer surface of the hollow core 502. In other embodiments, a polymeric sleeve is positioned over the hollow core 502 and secured to the hollow core 502 by an adhesive. The adhesive can include polymer, metal, composite based materials or combination. The adhesive can improve the bonding at the inner member 802 and the surface of the cylindrical hollow core 502 forming the interface 808. Although the inner member 802, which may also be referred to as a sleeve member, comprises a circular or cylindrical shape in the illustrated embodiment, the inner member 802 may comprise other shapes or profiles, including polygonal, elliptical, and/or combinations thereof.

Referring to FIGS. 8B and 8C, the interface 808 comprises a recess in the outer surface of the cylindrical hollow core 502, the inner member 802 is positioned within the recess so that an outer surface of the inner member 802 is flush with the outer surface 526 of the cylindrical hollow core 502, forming a smooth, or continuous outer profile of the combined hollow core 502 and inner member 802. In that regard, the inner member 802 is continuous with the proximal and distal portions of the hollow member 502 so that they together form a continuous outer surface. The recesses 808, 706 are formed such that they do not extend into the lumen 528 of the hollow core 502. In other embodiments, the cylindrical hollow core 502 is not formed with a recess and the inner member 802 is positioned over the outer surface of the cylindrical hollow core 502 such that it is not flush with the outer surface 526 of the cylindrical hollow core 502. In some aspects, the inclusion of the inner member 802 may provide improved acoustic properties and performance of the scanner assembly (e.g. backscattering and/or attenuation). The material and the thickness 810 of the inner member 802 may be selected to attain desired acoustic properties at the distal portion 512 of the chassis 800. For example, the thickness 810 may range between 0.0004-0.006 inches, and the material may comprise a polymer material such as Pebax® or polyimide.

Alternatively, an additional matching material may be incorporated at the interface between the inner member 802 and the cylindrical hollow core 502 surface in order to improve acoustic energy transmission for the scanner assembly 110 and the chassis 800. The inner member 802 may also serve as a shock absorber for shock imposed on the scanner assembly by external or internal forces.

Figure 9A:
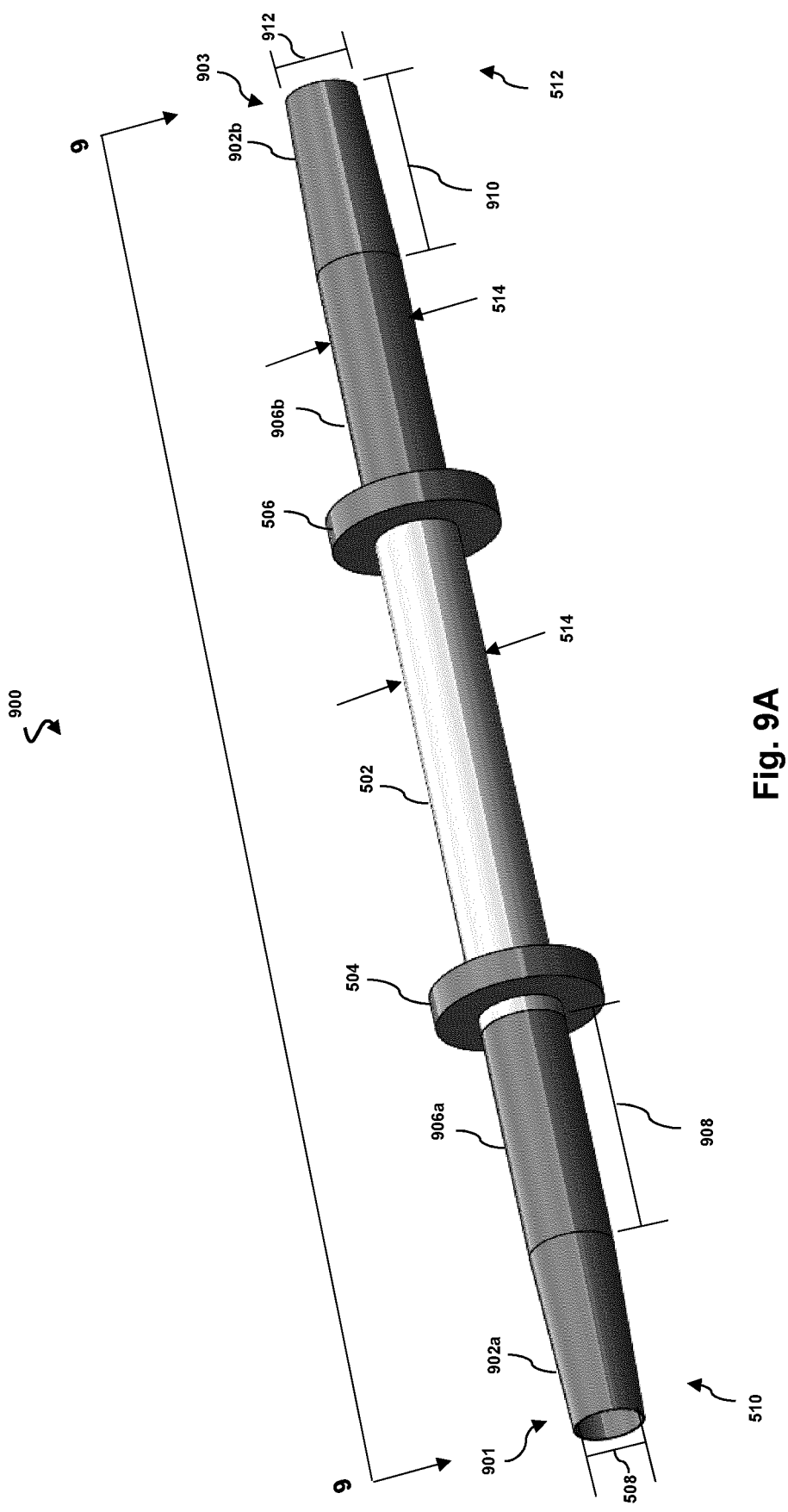
FIG. 9A is perspective view of a chassis of the scanner assembly including cylindrical hollow core with two polymeric rings and two flexible portions dressed partially on each end of the core and around its perimeter, according to aspects of the present disclosure.
Figure 9B:
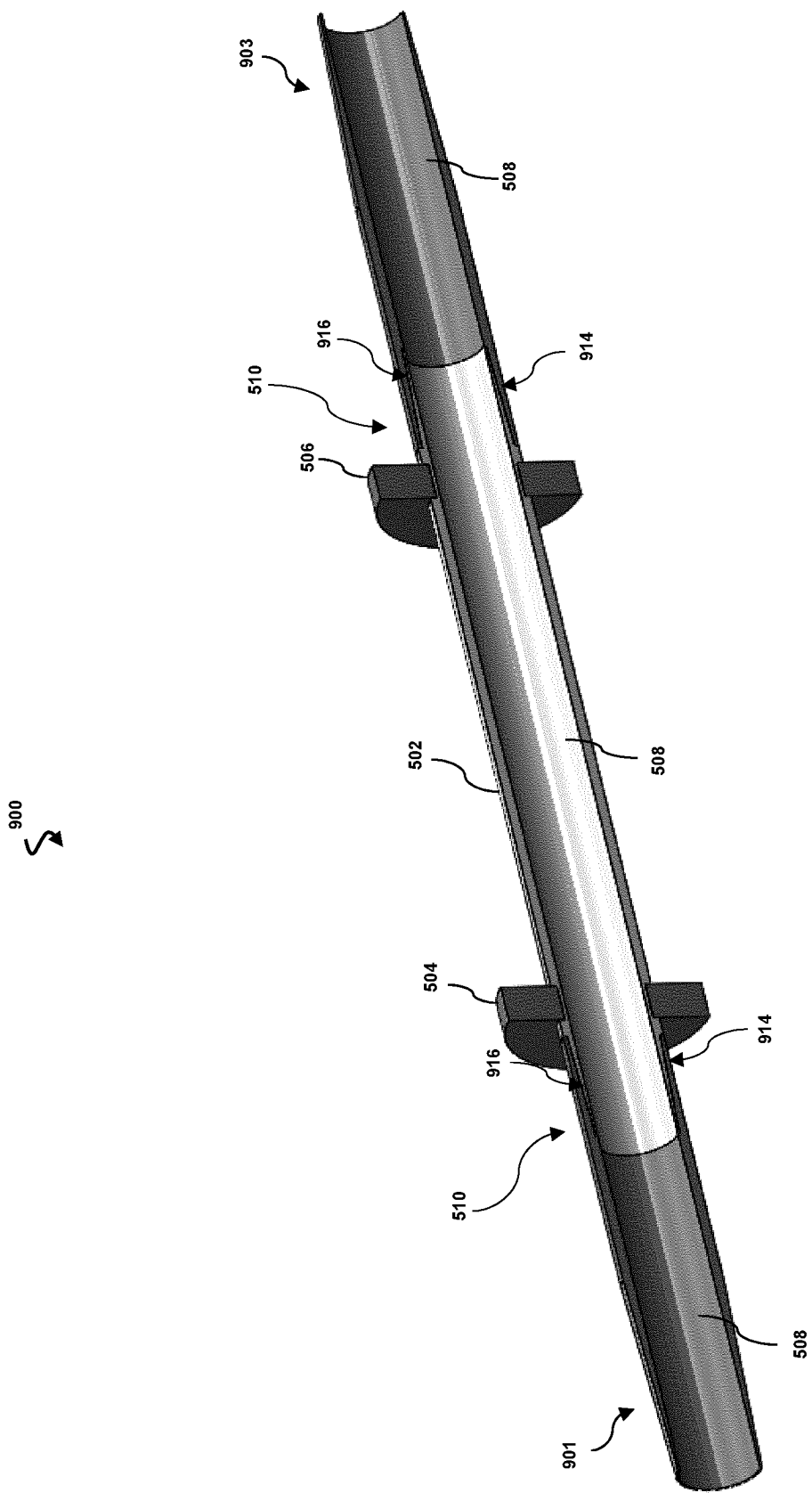
FIG. 9B is a perspective cross-sectional side view of the chassis shown in FIG. 9A taken along section line 9-9.

FIG. 9A is perspective view of a chassis 900 of a scanner assembly including the cylindrical hollow core 502, two polymeric rings 504, 506, a flexible component 901 positioned at the proximal end 510, and a flexible component 903 positioned at the distal end 512 of the hollow core 502 and around its perimeter. The flexible component 901 may be referred to as a proximal tubular member, and the flexible component 903 may be referred to as a distal tubular member 903. FIG. 9B is a perspective cross-sectional view of the chassis 900 shown in FIG. 9A taken along section line 9-9. The chassis 900 may include some features and dimensions similar or identical to the chassis 500 of FIG. 5, including the hollow core 502 and the polymeric rings 504, 506. The chassis 900 shown in FIGS. 9A and 9B further includes opposing flexible components 901, 903 on the proximal end 510 and distal end 512 of the cylindrical hollow core 502, respectively. The flexible component 901 comprises a tapered section 902a and a cylindrical section 906a, together forming the flexible component 901 as an integral component. Similarly, the flexible component 903 comprises a tapered section 902b and a cylindrical section 906b, together forming the flexible component 903 as an integral component. The tapered sections 902a and 902b shown in FIGS. 9A and 9B comprise a tapering of the outer surface of the flexible components 901, 903, such that an inner diameter of each of the flexible components 901, 903 remains constant or substantially constant across its length while the outer diameter decreases across its length. In other embodiments, the tapered sections 906a, 906b comprise a tapering of the outer and inner surfaces of the flexible components 901, 903. In other embodiments, the flexible components comprise a cylindrical shape along their entire lengths, and do not comprise tapered sections.

The flexible components 901, 903 are coupled or attached to the hollow core 502 proximate to the respective ends of the hollow core 502, and proximate to the respective polymeric rings 504, 506. Each of the cylindrical sections 906a, 906b includes an outer diameter 514, which may range between 0.036-0.037 inches, and may be substantially equal in diameter as the hollow core 502. Each of the cylindrical sections 906a, 906b includes a length 908, which may range between 0.030-0.033 inches. The tapered sections 902a, 902b have end diameters 912, which may be smaller than the diameter 514 of the hollow core 502, and may range between 0.021-0.022 inches. The tapered sections have a length 910, which may range between 0.10-0.030 inches. The smaller diameter 912 may increase flexibility on each end 510, 512 as a result of thinner sidewalls. In some aspects, the dimensions and values provided herein may be suitable for a catheter that accommodates a guidewire of up to 0.014 inches. However, it will be understood that these values are only exemplary and are not intended to limit the scope of the present disclosure. For example, the dimensions provided herein could be modified to accommodate guidewires or intraluminal devices of other sizes. For example, in some embodiments, the dimensions and values provided herein could be modified to accommodate a guidewire of up to 0.035 inches. Still other ranges are contemplated. For example, one or more of the exemplary dimensions provided above could be increased or decreased according to different diagnostic applications. For example, one or more of the dimensions provided above could be modified by 0.5×, 1.5×, 2×, 3×, 5×, or any other suitable multiplier.

The presence of the flexible components 901, 903 may advantageously allow for a gradual transition in stiffness from the rigid stainless steel cylindrical member 502 to a flexible catheter and the, which may reduce the chance of kinking or damage to the intraluminal catheter. The flexible member 901 at the proximal end 510 of the chassis 900 may be coupled or attached to the inner and/or outer members of the catheter by one or more techniques, including thermal bonding, adhesives, interference fit, etc., and may function as a strain relief and/or a transition in rigidity from the. The flexible member 903 at the distal end 512 of the chassis 900 may be coupled to attached to the hollow core 502 by one more techniques, including over molding, thermal bonding, adhesives, doping, coating, interference fit, etc., and may function as a transition in stiffness for the catheter tip. In the embodiment shown in FIGS. 9A and 9B, the flexible components 901, 903 are attached to the cylindrical hollow core 502 at each end 510, 512, such that the inner diameter 508 of the cylindrical hollow core 502 is constant or uniform across their respective lengths. The attachment of the flexible components 901, 903 to the hollow core 502 forms interfaces 914, 916 comprising respective mating surfaces between the metal core 502 and the flexible components 901, 903. In some aspects, the interfaces or attachments of the flexible components 901, 903 may include other features, including recesses, grooves, holes, textured surfaces, and/or tapered surfaces that may improve mechanical strength and bonding. The chassis 900 advantageously includes multiple materials that may improve the functionality and mechanical performance of the device. For example, in some embodiments, a flexible component (e.g., 903) over molded onto the hollow core 502 may replace a separate distal tip member as shown above in FIG. 1A, for example. In some embodiments, the surface finish of the inner lumen of the flexible components 901, 903 may be selected to minimize friction with the guide wire.

Figure 10A:
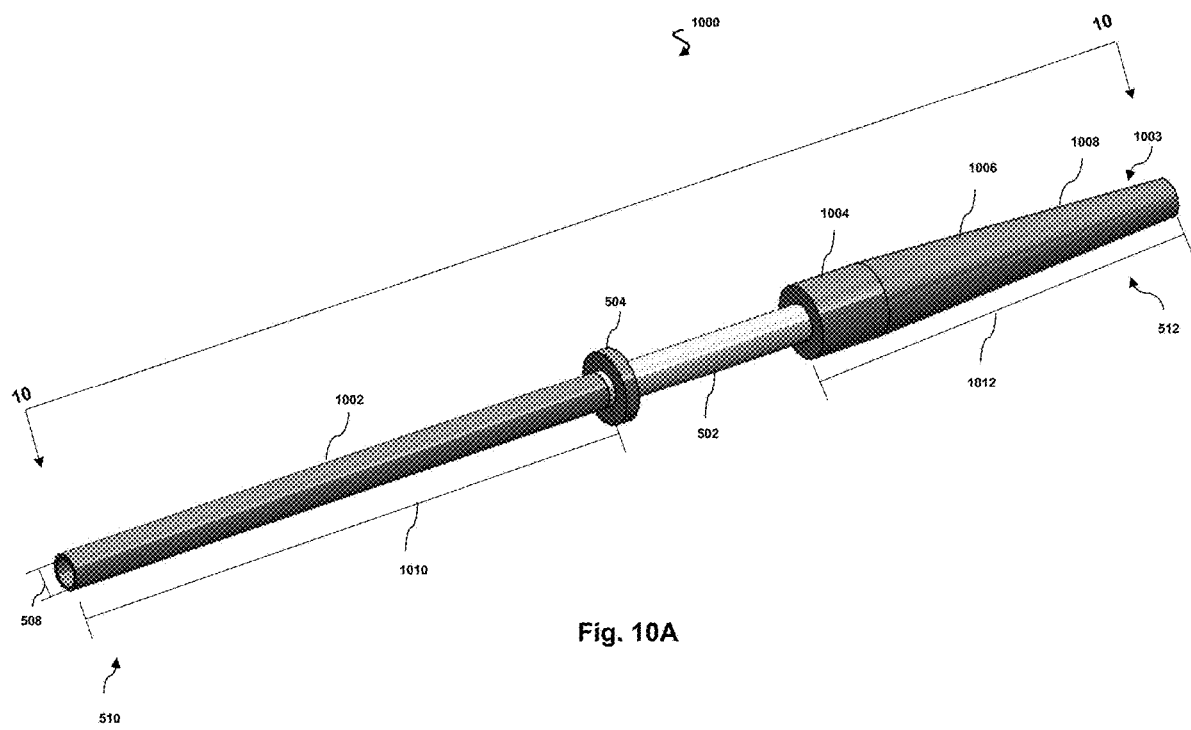
FIG. 10A is perspective view of a chassis of a scanner assembly including a cylindrical hollow core with two polymeric rings attached around its perimeter, and flexible portions positioned on each end of the hollow core, according to aspects of the present disclosure.
Figure 10B:
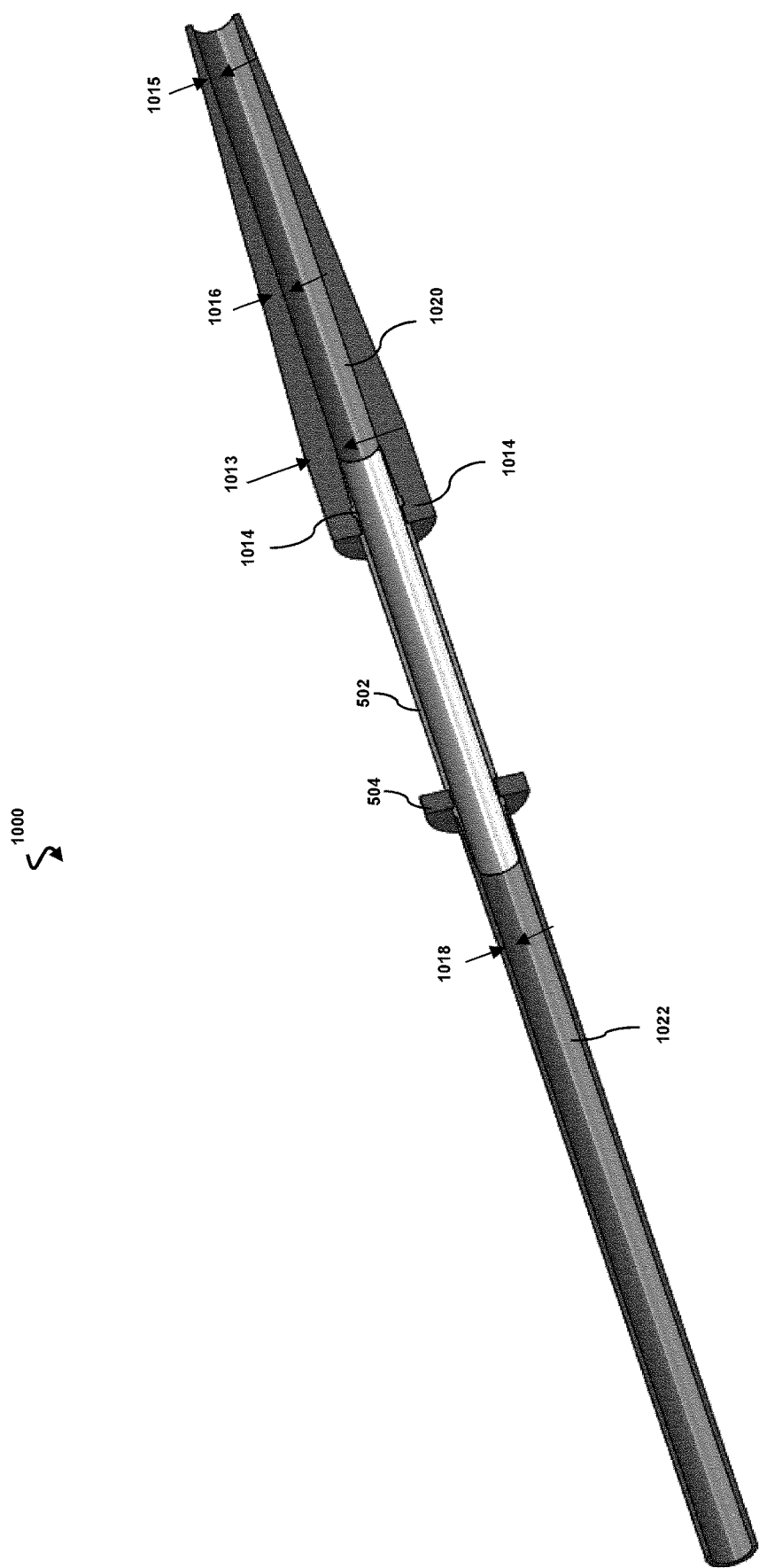
FIG. 10B is a perspective cross-sectional side view of the chassis shown in FIG. 10A taken along section line 10-10.

FIG. 10A is a perspective view of a chassis 1000 of a scanner assembly including a cylindrical hollow core 502 with a polymeric ring 504 and a flexible component 1003 positioned around a perimeter of the hollow core 502. FIG. 10B is a perspective cross-sectional view of the chassis 1000 shown in FIG. 10A taken along section line 10-10. The chassis 1000 may include features and/or dimensions similar or identical to the chassis 900 of FIGS. 9A and 9B, including a hollow core 502 and a ring member 504. In the embodiment of FIGS. 10A and 10B, the chassis 1000 is formed with a flexible component 1002 at the proximal end 510 and the flexible component 1003 at the distal end 512, where the flexible components comprise different geometries. In that regard, the flexible component 1003 comprises a generally cylindrical body that includes an annular or cylindrical section 1004 and a tapered or conical section 1006 forming an integral component. The flexible component 1003 may be referred to as a distal tip member. In some embodiments, the cylindrical section 1004 may comprise a shape and dimensions similar to the polymeric ring 504. For example, in some embodiments, the cylindrical section 1004 includes an outer diameter that is similar or identical to the polymeric ring 504. Flexible component 1003 comprises a length 1012, with the cylindrical section 1004 positioned around a distal portion of the hollow core 502, and the tapered section 1006 extending distally of the hollow core 502. Flexible component 1003 includes variable thicknesses 1013, 1015, 1016, along its length 1012 while maintaining uniform cross-sectional inner diameter 508 (as shown in FIGS. 10A and 10B). In that regard, the tapered section comprises a tapered outer surface such that the inner diameter 508 is constant along the length 1012. It will be understood that, in some embodiments, the inner surface may be tapered. In some embodiments, the outer surface is tapered while the thickness (1013, 1015, 1016) of the flexible component 1003 is constant along its length.

Referring to FIG. 10B, the flexible component 1003 may be attached to the outer surface of the cylindrical hollow core 502 by over molding, mechanical attachment, interference fit, and/or an adhesive, and may fit in and/or around features of the hollow inner member 502, including projections 1014. For example, the flexible member 1003 may include a slot or recess in an inner surface of the flexible member 1003 that is configured to fit over or around the projections 1014 of the inner hollow member to retain the flexible component 1003 in place. The unique attachment interface can improve adhesion of the flexible component 1003 to the hollow inner member 502 and achieve functional objectives similar to those described above for other structures explained in FIGS. 5-9. The flexible component 1003 includes an inner lumen 1020 in communication with, or extending from, the lumen of the core member 502, and may be configured to receive a guide wire.

At the proximal end 510, the chassis 1000 includes the flexible component 1002. In the illustrated embodiment, the flexible component 1002 includes a generally cylindrical body defining a lumen 1022 that includes a uniform on constant diameter along its length, and an outer profile that is uniform or constant along its length. A distal portion of the flexible component 1002 is formed or positioned around the proximal end of the cylindrical hollow core 502, the flexible component 1002 is formed with optimized uniform thickness 1018 and length 1010 in order to achieve flexibility, radiopacity, acoustics and other properties to meet desired functional objectives.

FIG. 11 is a perspective cross-sectional side view of a chassis 1100 of a scanner assembly including cylindrical hollow core 502 where the polymer ring 504 is attached around its perimeter using a lock-in feature or projection 1101. In the chassis 1100 of FIG. 11, the polymer ring 504 is attached to the surface of the cylindrical hollow core 502 by positioning the polymeric ring 504 over the corresponding projection 1102. The projection 1102 may be positioned, locked-in, or press-fit into a corresponding recess or slot in the inner surface of the polymeric ring 504. In some embodiments, the attachment shown in FIG. 11 may be achieved by forming the projections 1102 on the hollow core 502, and over molding the polymer ring 504 over the projection. This structural joining method can be applied to any of the structural embodiments presented above.

To fabricate the variously chassis embodiments disclosed herein, several different traditional and non-traditional manufacturing techniques may be used based on material, features and structure of the chassis, including injection molding, casting, 3D printing, laser cutting and texturing, extrusion, micro-machining, co-forming, re-flow, electron beam melting and/or other suitable techniques. It should be understood that no limitation to any particular manufacturing technology is intended or should be implied from the teachings of the disclosed principles.

The structure of the embodiments described above may be selected based on the size, functional objective, and/or type of scanner assembly. Thus, any advantageous structural arrangement with appropriate length, width, and height, may be employed, which could include not only the circular/cylindrical and semi-circular shapes discussed herein, but also triangular, conic, polygon and rectilinear shapes may also be employed. The chassis may include any number of polymeric rings such as one, two, three, five, ten, or any other suitable number, both greater and smaller. Further, the chassis may include variety of combinations of the features described above. All exemplary variations of the chassis from FIGS. 5-11 may be coupled to a scanner assembly. The chassis advantageously incorporates variety of material properties and structures that can improve performance characteristics for a variety of catheters and intraluminal devices. In that regard, although the embodiments shown in FIGS. 5A-11 are described with respect to IVUS imaging catheters, it will be understood that the support member or chassis described above may be used with a variety of intraluminal devices, including intracardiac echocardiography (ICE) catheters, optical coherence tomography (OCT) catheters, sensing catheters, guide catheters, sensing guidewires, or any other suitable type of intraluminal device.

Figure 12:
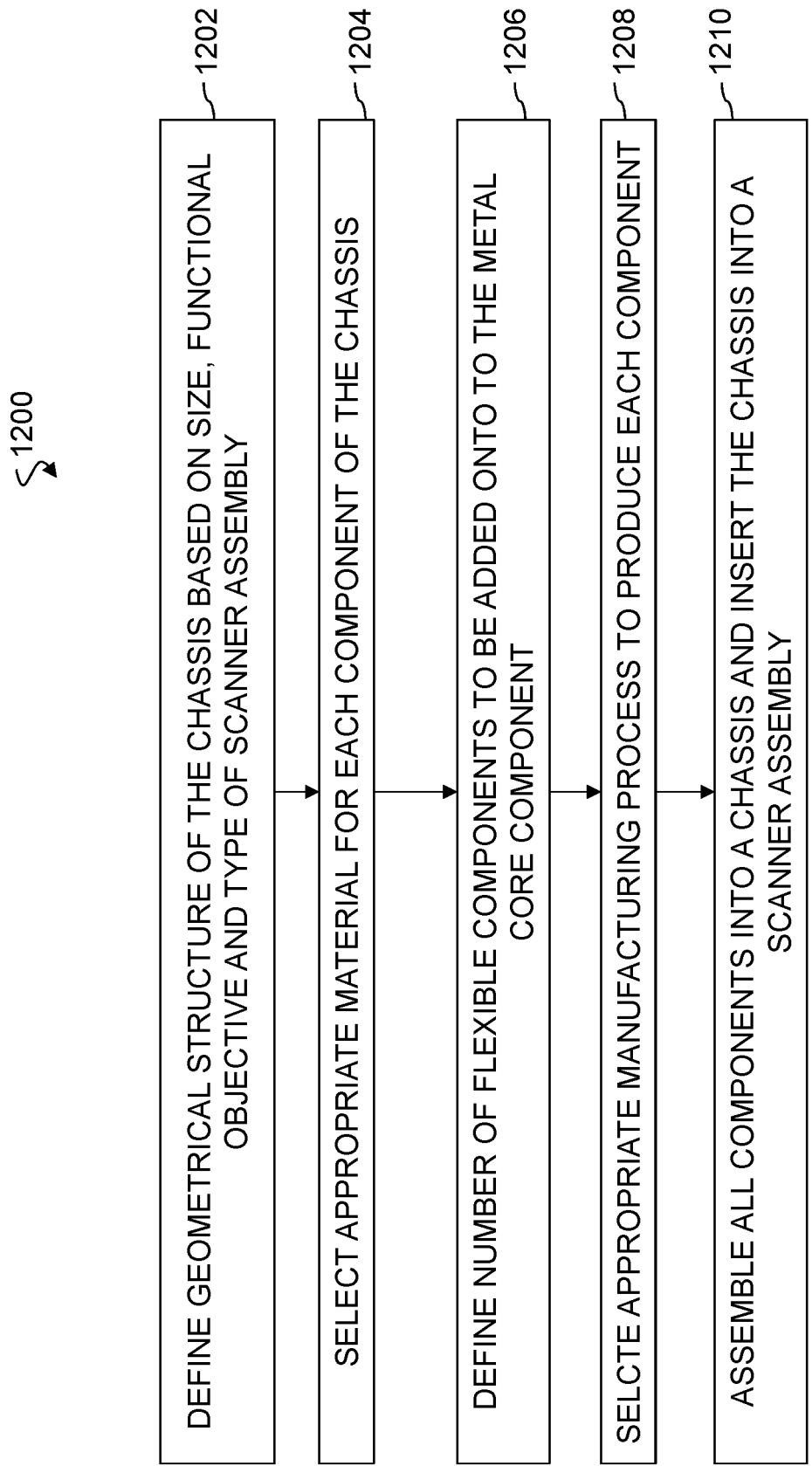
FIG. 12 is a flow diagram of a method of forming a multi-material chassis for a scanner assembly, according to aspects of the disclosure.

FIG. 12 illustrates a flow diagram illustrating an exemplary method 1200 of forming a scanner assembly with a multi-material chassis. At step 1202, the method 1200 includes defining a geometrical structure of the chassis for the type of scanner to be used and the desired functional objective. As shown in FIGS. 5-11, variety of structural geometries can compose the chassis based on the desired functionality.

At step 1204, the method 1200 includes selecting an appropriate material for each component of the chassis. The material is selected based on the desired properties that the scanner assembly needs such as rigidity, opacity, flexibility, acoustic, machinability, mold-ability and combination thereof.

At step 1206, the method 1200 includes defining the number of flexible components to be attached to a hollow core that will produce the desired functionality of the scanner assembly. This step 1206 may include adding two or more polymer rings, a combination of two polymer rings and a flexible inner member, a polymer ring and a flexible component that serves as guidewire or any combination thereof.

At step 1208, the method 1200 includes selecting a suitable manufacturing process to produce each component of the multi-material chassis such as selecting micro-machining to form hollow core component, selecting an over molding process to form the polymer rings over the hollow core component, and any other suitable manufacturing process corresponding to each component of the chassis.

At step 1210, the method 1200 includes connecting all components to form the multi-material chassis. For example, in some embodiments the flexible components can be placed into a recess formed on the surface of the hollow core member, the flexible components can be press-fit into the hollow core member, or they can be applied via over molding as shown in FIGS. 5-11. At step 1210, once the multi-material chassis is formed it may be coupled to the scanner assembly.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal ultrasound imaging catheter, comprising:
   a flexible elongate member configured to be positioned within a body lumen of a patient;
   a support member coupled to a distal portion of the flexible elongate member, wherein the support member comprises:
      a hollow inner member comprising a first material; and
      a first annular member positioned around a perimeter of the hollow inner member at a proximal portion of the hollow inner member, wherein the first annular member extends radially outward from the hollow inner member, and wherein the first annular member comprises a second material that is different from the first material; and
   an ultrasound scanner assembly configured to obtain ultrasound imaging data of the body lumen, wherein the ultrasound scanner assembly comprises a flexible substrate positioned around the first annular member such that the flexible substrate is distinct from the first annular member.

2. The intraluminal ultrasound imaging catheter of claim 1, wherein the hollow inner member comprises a cylindrical shape.

3. The intraluminal ultrasound imaging catheter of claim 2, wherein the hollow inner member comprises a uniform outer surface and a uniform inner surface.

4. The intraluminal ultrasound imaging catheter of claim 2,
   wherein the hollow inner member comprises an outer surface with a first recess, wherein the first recess is formed at the proximal portion of the hollow inner member such that the second material of the first annular member is positioned within the first recess.

5. The intraluminal ultrasound imaging catheter of claim 1, wherein the first material of the hollow inner member comprises a metal and the second material of the first annular member comprises a polymer.

6. The intraluminal ultrasound imaging catheter of claim 5, wherein the second material is over molded onto the hollow inner member.

7. The intraluminal ultrasound imaging catheter of claim 1, wherein the first annular member comprises a ring shape.

8. The intraluminal ultrasound imaging catheter of claim 1, wherein the first annular member comprises a polygonal shape.

9. The intraluminal ultrasound imaging catheter of claim 1, wherein the hollow inner member and the first annular member are coupled by an adhesive at the proximal portion of the hollow inner member.

10. The intraluminal ultrasound imaging catheter of claim 9, wherein the adhesive comprises a polymer material.

11. The intraluminal ultrasound imaging catheter of claim 1,
wherein the support member further comprises a sleeve member positioned around the perimeter of the hollow inner member at an intermediate portion of the inner hollow member,
wherein the sleeve member is positioned distal of the first annular member, and
wherein the sleeve member comprises a third material.

12. The intraluminal ultrasound imaging catheter of claim 11,
wherein the hollow inner member comprises an outer surface with a second recess,
wherein the second recess is formed at the intermediate portion of the hollow inner member such that the sleeve member is positioned within the second recess to form a continuous outer profile with the hollow inner member.

13. The intraluminal ultrasound imaging catheter of claim 11, wherein the third material of the sleeve member comprises a polymer.

14. The intraluminal ultrasound imaging catheter of claim 11,
wherein the support member further comprises a second annular member positioned around the perimeter of the hollow inner member at a distal portion of the hollow inner member,
wherein the second annular member extends radially outward from the hollow inner member,
wherein the flexible substrate is positioned around the second annular member.

15. The intraluminal ultrasound imaging catheter of claim 14,
wherein the second annular member comprises the second material, and
wherein the second annular member comprises a ring shape.

16. The intraluminal ultrasound imaging catheter of claim 14,
wherein the support member further comprises a distal tubular member extending distally of the hollow inner member, and
wherein the second annular member and the distal tubular member comprise a flexible third material.

17. The intraluminal ultrasound imaging catheter of claim 14, wherein the first annular member, the sleeve member, and the second annular member form an integral component positioned around the perimeter of the hollow inner member.

18. The intraluminal ultrasound imaging catheter of claim 1, wherein a sidewall of the hollow inner member comprises at least one of a groove or a through-hole.

19. The intraluminal ultrasound imaging catheter of claim 1, further comprising:
a proximal tubular member coupled to the proximal portion of the hollow inner member and extending proximally of the hollow inner member; and
a distal tip member coupled to a distal portion end of the hollow inner member and extending distally of the hollow inner member, wherein the distal tip member comprises:
an annular section positioned around the perimeter of the hollow inner member at a distal portion of the hollow inner member, wherein the annular section extends radially outward from the hollow inner member; and
a tapered section extending distally of the annular section,
wherein the proximal tubular member and the distal tip member comprise a polymer material.

20. An intraluminal ultrasound imaging system, comprising:
an intraluminal ultrasound imaging catheter, comprising:
a flexible elongate member configured to be positioned within a body lumen of a patient;
a support member coupled to a distal portion of the flexible elongate member, wherein the support member comprises:
a metallic, hollow inner member comprising a first material;
a polymeric ring positioned around a perimeter of the hollow inner member at a proximal portion of the hollow inner member, wherein the polymeric ring extends radially outward from the hollow inner member; and
an ultrasound scanner assembly configured to obtain ultrasound imaging data of the body lumen, wherein the ultrasound scanner assembly comprises a flexible substrate positioned around the polymeric ring such that the flexible substrate is distinct from the polymeric ring; and
a processor circuit in communication with the intraluminal ultrasound imaging catheter, wherein the processor circuit is configured to generate an intraluminal ultrasound image using the ultrasound imaging data and output the intraluminal ultrasound image to a display.

21. The intraluminal ultrasound imaging catheter of claim 1,
wherein the support member further comprises a second annular member positioned around the perimeter of the hollow inner member at a distal portion of the hollow inner member,
wherein the second annular member extends radially outward from the hollow inner member,
wherein the flexible substrate is positioned around the second annular member.

22. The intraluminal ultrasound imaging catheter of claim 1, wherein the hollow inner member extends:
proximal of the first annular member such that the first annular member is spaced from a proximal end of the hollow inner member; and distal of the second annular member such that the second annular member is spaced from a distal end of the hollow inner member.

* * * * *